United States Patent
Murer

(10) Patent No.: US 6,900,280 B2
(45) Date of Patent: May 31, 2005

(54) ACID MACROMONOMERS AND THEIR METHOD OF PREPARATION

(75) Inventor: Peter Murer, Allschwil (CH)

(73) Assignee: CIBA Specialty Chemicals Corp., Tarrytown, NY (US)

(*) Notice: Subject to any disclaimer, the term of this patent is extended or adjusted under 35 U.S.C. 154(b) by 0 days.

(21) Appl. No.: 10/469,182
(22) PCT Filed: Feb. 21, 2002
(86) PCT No.: PCT/EP02/01852
§ 371 (c)(1),
(2), (4) Date: Aug. 26, 2003
(87) PCT Pub. No.: WO02/079271
PCT Pub. Date: Oct. 10, 2002

(65) Prior Publication Data
US 2004/0072978 A1 Apr. 15, 2004

(30) Foreign Application Priority Data
Mar. 1, 2001 (EP) .......................... 01810208

(51) Int. Cl.$^7$ .............................. C08F 120/06
(52) U.S. Cl. .................... 526/317.1; 526/193; 526/217; 526/222; 526/256; 526/258; 526/263; 526/307.6; 526/318.2; 526/318.3; 526/328.5; 526/338; 526/342; 526/347.1; 526/348.7
(58) Field of Search .................... 526/256, 258, 526/263, 274, 286, 310, 317.1, 318.2, 318.3, 193, 219, 222, 328.5, 338, 342, 347.1, 348.7

(56) References Cited

U.S. PATENT DOCUMENTS 5,721,330 A 2/1998 Ma ..................... 526/318.41
6,576,684 B1 * 6/2003 Desobry et al. ........... 522/167

FOREIGN PATENT DOCUMENTS

WO 96/15157 5/1996
WO 00/11041 3/2000

* cited by examiner

Primary Examiner—Helen L. Pezzuto
(74) Attorney, Agent, or Firm—Tyler A. Stevenson

(57) ABSTRACT

The invention relates to a composition comprising: a) an acid monomer or oligomer of acrylic acid or of an acid derivative of acrylic acid or mixtures thereof; or a mixture of an ethylenically unsaturated monomer or oligomer and an acid monomer or oligomer of acrylic acid or of an acid derivative of acrylic acid; b) at least one radical initiator which forms a radical upon heating or upon irradiation with (UV) light in the range from 305 nm to 450 nm; and c) a compound of the formulae (I), (Ib) or (Ic) wherein Y represents a group that activates nucleophilic addition reactions at the adjacent double bond; X represents halogen or the anion of an aliphatic or aromatic monocarboxylic or dicarboxylic acid of 1–12 carbon atoms, of a monovalent or divalent oxo acid or of a complex acid; n represents 0 or 1; $R_1$, $R_2$, $R_3$ independently of one another represent hydrogen, $C_1$–$C_{18}$alkyl, $C_3$–$C_{18}$alkyl interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$ cycloalkyl and $C_3$–$C_{12}$cycloalkyl containing at least one nitrogen or oxygen atom, which are substituted with at least one substituent selected from the group consisting of $NO_2$, halogen, amino, hydroxy, cyano, carboxy, $C_1$–$C_4$alkoxy, $C_1C_4$alkylthio, $C_1C_4$alkylamino, di($C_1$–$C_4$alkyl)amino and —O—C(=O)—$C_1C_{18}$alkyl; or phenyl or naphthyl or phenyl and naphthyl substituted with at least one substituent selected from the group consisting of $C_1$–$C_4$alkyl, $C_1$–$C_4$alkoxy, $C_1C_4$alkylthio, halogen, cyano, hydroxy, carboxy, $C_1$–$C_4$alkylamino and di)$C_1$–$C_4$alkyl)amino; or $R_1$ and $R_2$ together with the linking N, P or S-heteroatoms form a $C_3$–$C_{12}$ heteroycloalkyl radical; or $R_1$ and $R_2$ together form the groups: (Id); or (Ie) $R_1$, $R_2$ and $R_3$ together form the groups (If) or (Ig). The invention relates also to acid macromers and to their method of preparation by radically initiated polymerization.

10 Claims, No Drawings

ACID MACROMONOMERS AND THEIR METHOD OF PREPARATION

The invention relates to novel compositions of acid macromonomers having terminal vinyl or dienyl groups, a controlled degree of polymerisation and a low polydispersity. The invention also relates to their method of preparation by radically initiated polymerisation.

U.S. Pat. No. 5,727,330 discloses compositions of macromonomers having a very high content of acid monomers and comonomers containing polyoxyethylene glycol groups. The acid monomer and the comonomer are radically polymerised in the presence of a cobalt complex as chain transfer agent.

The published International Patent Application (WO) WO 96/15157 describes a process for the synthesis of vinyl terminated block polymers, homopolymers and copolymers by contacting vinyl monomers, vinyl terminated compounds and free radicals derived from common initiators.

The use of addition fragmentation agents (AFA) for the control of the degree of polymerisation is known and a variety of compounds have already been suggested, cf. Colombani et al. in "*Addition Fragmentation Processes in Free Radical Polymerisation*", *Prog. Polym. Sci.*, Vol. 21, 439–503, 1996.

Y. Yagci et al. disclose the use of allylic sulphonium and ammonium salts, in particular pyridinium and allyloxypyridinium salts, in photochemically and thermally generated radical promoted cationic polymerisation. References are, for example, *Polymer* Vol. 36, 3093–3098 (1995) and *React. Funct. Polym.* Vol. 42, 255–264 (1999).

WO 00/11041 discloses specific allyl or dienyl cationic addition fragmentation agents, which are highly efficient in thermally and in photochemically induced controlled radical polymerisation.

New Compositions

The present invention relates to a composition comprising a) an acid monomer or oligomer of acrylic acid or of an acid derivative of acrylic acid or mixtures thereof; or
a mixture of an ethylenically unsaturated monomer or oligomer and an acid monomer or oligomer of acrylic acid or of an acid derivative of acrylic acid;
b) at least one radical initiator which forms a radical upon heating or upon irradiation with (UV) light in the range from 305 nm to 450 nm; and
c) a compound of the formulae (Ia), (Ib) or (Ic)

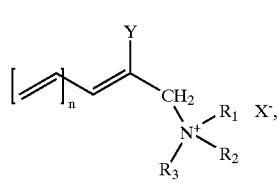
(Ia)

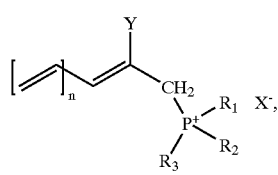
(Ib)

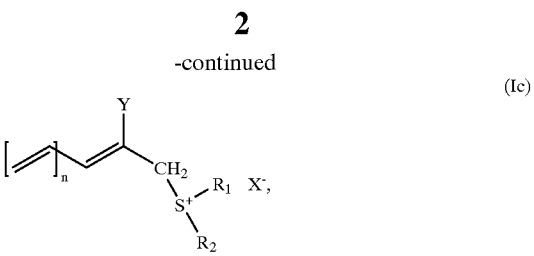
(Ic)

wherein

Y represents a group that activates nucleophilic addition reactions at the adjacent double bond;

$X^-$ represents halogen or the anion of an aliphatic or aromatic monocarboxylic or dicarboxylic acid of 1–12 carbon atoms, of a monovalent or divalent oxo acid or of a complex acid;

n represents 0 or 1;

$R_1$, $R_2$, $R_3$ independently of one another represent hydrogen, $C_1$–$C_{18}$alkyl, $C_3$–$C_{18}$alkyl interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_3$–$C_{18}$alkyl interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl and $C_3$–$C_{12}$cycloalkyl containing at least one nitrogen or oxygen atom, which are substituted with at least one substituent selected from the group consisting of $NO_2$, halogen, amino, hydroxy, cyano, carboxy, $C_1$–$C_4$alkoxy, $C_1$–$C_4$alkylthio, $C_1$–$C_4$alkylamino, di($C_1$–$C_4$alkyl)amino and —O—C(=O)—$C_1$–$C_{18}$alkyl; or phenyl or naphthyl or phenyl and naphthyl substituted with at least one substituent selected from the group consisting of $C_1$–$C_4$alkyl, $C_1$–$C_4$alkoxy, $C_1$–$C_4$alkylthio, halogen, cyano, hydroxy, carboxy, $C_1$–$C_4$alkylamino and di($C_1$–$C_4$alkyl)amino; or $R_1$ and $R_2$ together with the linking N, P or S-heteroatoms form a $C_3$–$C_{12}$ heterocycloalkyl radical; or $R_1$ and $R_2$ together form the groups:

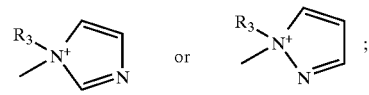

or $R_1$, $R_2$ and $R_3$ together form the groups

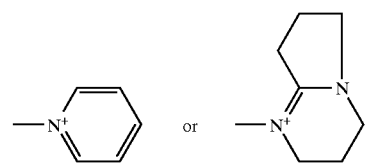

Preferred are compounds of the formula (Ia) with n=1.

1. Definitions with Regard to the Addition Fragmentation Agents of the Formulae (Ia). (Ib) and (Ic)

1.1 Residues $R_1$, $R_2$ and $R_3$

The alkyl radicals in the various substituents are straight chained or, if possible, branched carbon chains. Examples of $C_1$–$C_{18}$alkyl are methyl, ethyl, n-propyl, isopropyl, n-butyl, 2-butyl, isobutyl, t-butyl, n-pentyl, 2-pentyl, neopentyl, n-hexyl, n-heptyl, n-octyl, 2-ethylhexyl, t-octyl or straight chained nonyl, decyl, undecyl, dodecyl, tridecyl, tetradecyl, hexadecyl or octadecyl.

$C_3$–$C_{18}$Alkenyl is straight chained or branched, if possible, e.g. propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl.

Preferred is alkenyl with 3 to 12, particularly preferred with 3 to 6 carbon atoms.

$C_3$–$C_{18}$Alkynyl is straight chained or branched, for example 2-propynyl, 2-butynyl, 3-butynyl, n-2-octynyl, or n-2-octadecynyl.

Preferred is alkynyl with 3 to 12, particularly preferred with 3 to 6 carbon atoms.

$C_3$–$C_{12}$Cycloalkyl is, typically, cyclopropyl, cyclobutyl, cyclopentyl, methylcyclopentyl, dimethylcyclopentyl, cyclohexyl or methylcyclohexyl.

Cycloalkyl which is interrupted by at least one O or N atom is, for example, 2-tetrahydropyranyl, tetrahydrofuryl, 1,4-dioxanyl, pyrrolidinyl, tetrahydrothienyl, pyrazolidinyl, imidazolidinyl, butyrolactonyl, caprolactamyl.

$C_7$–$C_9$Phenylalkyl is, for example, benzyl, 1- or 2-phenylethyl or 1-or 2-phenylpropyl.

$C_3$–$C_{18}$Alkyl interrupted by at least one O atom corresponds to the partial formula —$((CH_2)_a$—$O)_bR$, wherein a is a numeral from 1 to 6 and b is a numeral from 2 to 10, and R represents hydrogen or methyl, for example —$CH_2$—$CH_2$—$O$—$CH_2$—$CH_3$, —$CH_2$—$CH_2$—$O$—$CH_3$ or —$CH_2$—$CH_2$—$O$—$CH_2$—$CH_2$—$CH_2$—$O$—$CH_2$—$CH_3$. It is preferably derived from polyethylene glycol.

Halogen is fluorine, chlorine, bromine or iodine, preferably chlorine or bromine.

Preferably $R_1$, $R_2$, $R_3$ independently of one another represent $C_1$–$C_{18}$alkyl, $C_3$–$C_{18}$alkyl interrupted by at least one nitrogen or oxygen atom, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_3$–$C_{18}$alkyl interrupted by at least one nitrogen or oxygen atom, $C_7$–$C_9$phenylalkyl, $C_3$–$C_{12}$cycloalkyl and $C_3$–$C_{12}$cycloalkyl containing at least one nitrogen or oxygen atom, which are substituted with at least one substituent selected from the group consisting of $NO_2$, halogen, amino, hydroxy, cyano, carboxy, $C_1$–$C_4$alkoxy, $C_1$–$C_4$alkylthio, $C_1$–$C_4$alkylamino and di($C_1$–$C_4$alkyl)amino; or phenyl, or phenyl substituted with at least one substituent selected from the group consisting of $C_1$–$C_4$alkyl, $C_1$–$C_4$alkoxy, $C_1$–$C_4$alkylthio, halogen, cyano, hydroxy, carboxy, $C_1$–$C_4$alkylamino and di($C_1$–$C_4$alkyl)amino; or $R_1$ and $R_2$, together with the linking N, P or S-heteroatoms, form a $C_4$–$C_7$heterocycloalkyl radical; or $R_1$ and $R_2$ together form the groups

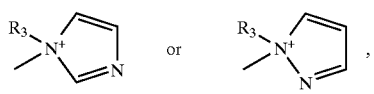

or $R_1$, $R_2$ and $R_3$ form the groups

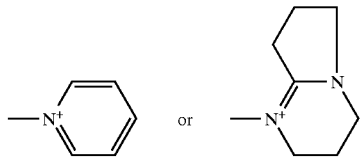

More preferably $R_1$, $R_2$, $R_3$ independently of one another represent $C_1$–$C_{12}$alkyl, $C_1$–$C_{12}$alkyl substituted by cyano or hydroxy, $C_3$–$C_{12}$alkyl interrupted by at least one nitrogen or oxygen atom, benzyl or phenyl, or benzyl and phenyl which are substituted by at least one substituent selected from the group consisting of $C_1$–$C_4$alkyl, $C_1$–$C_4$alkoxy, $C_1$–$C_4$alkylthio, halogen, cyano, hydroxy and carboxy.

1.2 Group Y

In a compound of the formulae (Ia), (Ib) or (Ic) the group Y may be any substituent that activates or facilitates any type of nucleophilic addition reactions at the double bond, especially Michael type addition reactions.

Preferably Y represents CN; phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—C(=O)$OR_4$ with $R_4$ being hydrogen or $C_1$–$C_{18}$alkyl;

—C(=O)$R_5$ with $R_5$ being hydrogen, halogen, $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—C(=O)$NR_6R_7$ with $R_6$ and $R_7$ independently of one another being hydrogen or $C_1$–$C_{18}$alkyl;

—S(=O)$R_8$ with $R_8$ being $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—S(=O)$_2R_9$ with $R_9$ being hydroxy, $C_1$–$C_{18}$alkyl, $C_1$–$C_{18}$alkoxy, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—P(=O)$R_{10}R_{11}$ with $R_{10}$ and $R_{11}$ independently of one another being $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen) nitro, cyano, hydroxy, carboxy, $C_1$–$C_4$alkylamino and di($C_1$–$C_4$alkyl)amino;

—P(=O)(OR$_{12}$)$_2$ with $R_{12}$ being $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—P(=O)OH(NR$_{13}R_{14}$)$_2$ with $R_{13}$ and $R_{14}$ independently of one another being $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl) amino.

Preferably Y represents CN, —C(=O)OR$_4$, phenyl or phenyl substituted by at least one substituent selected from the group consisting of C$_1$–C$_4$alkyl, C$_1$–C$_4$alkoxy, C$_1$–C$_4$alkylthio, halogen, cyano, hydroxy, carboxy, C$_1$–C$_4$alkylamino and di(C$_1$–C$_4$alkyl)amino and R$_4$ represents C$_1$–C$_8$alkyl.

Most preferably Y represents CN, —C(=O)OCH$_3$, —C(=O)OC$_2$H$_5$, phenyl or phenyl substituted by at least one substituent selected from the group consisting of C$_1$–C$_4$alkyl, C$_1$–C$_4$alkoxy, C$_1$–C$_4$alkylthio, halogen, nitro, cyano, hydroxy and carboxy.

1.3 Group X$^-$

X$^-$ represents halogen or the anion of an aliphatic or aromatic monocarboxylic or dicarboxylic acid from 1–12 carbon atoms, of a monovalent or divalent oxo acid or of a complex acid.

Examples of aliphatic monocarboxylic or dicarboxylic acids are formic, acetic, propionic, cyclohexane carbonic, mono-, di- or trichloroacetic acid, mono-, di- or trifluoroacetic, 1,2-, 1,3- or 1,4-cyclohexane dicarboxylic, succinic, glutaric and adipic acid and the like.

Examples of aromatic monocarboxylic or dicarboxylic acids are phenyl, benzoic, chloro-benzoic, phthalic, terephthalic, isophthalic, 4-naphthalene dicarboxylic, 2,6-naphthalene dicarboxylic and 4,4'-biphenyl dicarboxylic acid and the like.

Examples of monovalent or divalent oxo acids are perchloric, sulphuric, C$_1$–C$_{18}$alkylsulphonic, e.g. methanesulphonic acid or ethanesulphonic acid, fluorinated C$_1$–C$_{18}$alkylsulphonic, e.g. trifluoromethanesulphonic acid, benzenesulphonic, or 1- or 2-naphthalenesulphonic acid, or benzenesulphonic or 1- or 2-naphthalenesulphonic acid substituted with one or two substituents selected from the group consisting of C$_1$–C$_{12}$alkyl, e.g. p-toluenesulphonic acid, p-dodecylbenzenesulphonic acid or dimethylbenzenesulphonic acid, C$_1$–C$_{12}$alkoxy, C$_1$–C$_{12}$alkylthio, halogen, e.g. chlorobenzenesulphonic acid, nitro, hydroxy, carboxy, C$_1$–C$_4$alkylamino and di(C$_1$–C$_4$alkyl)amino; phosphoric, mono-C$_1$–C$_{18}$alkyl phosphoric, monophenyl phosphoric, di-C$_1$–C$_{18}$alkyl phosphoric, mono-C$_1$–C$_{18}$alkyl phosphonic and di-C$_1$–C$_{18}$alkyl phosphonic acid.

Benzenesulphonic acids substituted by two C$_1$–C$_{18}$ radicals refer to mixtures of o-, m- and p-substituted acids.

Examples of anions of complex acids are BF$_4^-$, B(Phenyl)$_4^-$, PF$_6^-$, SbCl$_6^-$, AsF$_6^-$ or SbF$_6^-$.

Further suitable anions are derived from alkyl-arylborates which are disclosed, for example, in U.S. Pat. No. 4,772,530, GB-A-2 307 474, GB-A-2 307 473, GB-A-2 307 472, and EP-A-0 775 706.

Examples are triphenyl-n-butylborate or the corresponding triphenylhexyl, triphenylmethyl, dimesityl-phenylmethyl- or -butyl, di(bromomesityl)-phenyl-methyl-or-butyl, tris(3-fluorophenyl)-hexyl, tris(3-fluorophenyl)-methyl- or -butyl, dichloromesityl-phenyl-methyl- or -butyl, tris(dichloromesityl)-methyl, tris(3-chlorophenyl)-hexyl, tris(3-chlorophenyl)-methyl- or -butyl, tris(3-bromphenyl)-hexyl, tris(3-bromphenyl)-methyl- or -butyl, tris(3,5-difluorophenyl)-hexyl, dimesityl-biphenyl-butyl, dimesityl-naphthylmethyl- or -butyl, di(o-tolyl)-9-anthracyl-methyl- or -butyl, or dimesityl-9-phenanthryl-phenyl- or -butylborate.

Preferably X$^-$ represents Cl$^-$, Br$^-$, I$^-$; ClO$_4^-$; CF$_3$SO$_3^-$, CH$_3$SO$_3^-$, CF$_3$COO$^-$, HSO$_4^-$, BF$_4^-$, B(Phenyl)$_4^-$, PF$_6^-$, SbCl$_6^-$, AsF$_6^-$ or SbF$_6^-$ or an anion derived from C$_1$–C$_{18}$alkylsulphonic acid, fluorinated C$_1$–C$_{18}$alkylsulphonic acid, benzenesulphonic acid, benzenesulphonic acid which is substituted by one or two radicals selected from the group consisting of C$_1$–C$_{12}$alkyl, e.g. p-toluenesulphonic acid, p-dodecyl benzenesulphonic acid or dimethylbenzenesulphonic acid, C$_1$–C$_{12}$alkoxy, C$_1$–C$_{12}$alkylthio, halogen, e.g. chlorobenzenesulphonic acid, nitro, hydroxy, carboxy, C$_1$–C$_4$alkylamino and di(C$_1$–C$_4$alkyl)amino.

More preferably X$^-$ represents Cl$^-$, Br$^-$, ClO$_4^-$, CF$_3$SO$_3^-$, CH$_3$SO$_3^-$, CF$_3$COO$^-$, BF$_4^-$, PF$_6^-$ or an anion derived from C$_1$–C$_{18}$alkylsulphonic acid, fluorinated C$_1$–C$_{18}$alkylsulphonic acid, benzenesulphonic acid, benzenesulphonic acid substituted by one or two C$_1$–C$_{18}$ alkyl radicals or chlorobenzenesulphonic acid.

2. Definition with Regard to the Acid Monomer

Acid derivatives of acrylic acid are, for example, alpha-substituted acrylic acid, and in particular, methacrylic acid, 2-(trifluoromethyl)propenoic acid, 2-(4-benzyloxy-3-methoxyphenyl)acrylic acid, 2-benzylacrylic acid, itaconic acid and derivatives thereof, or butene-1,2,3-tricarboxylic acid.

Derivatives of itaconic acid are for example monomethyl itaconate, monoethyl, mono-isopropyl, mono-n-butyl, mono-n-dodecyl, mono-2-ethylhexyl, monotrifluoroethyl, or monohexafluoroisopropyl itaconate.

The acid monomer is preferably acrylic acid or methacrylic acid.

3. Definitions of the Comonomer

Typically the ethylenically unsaturated monomer or oligomer which can be used as comonomer/cooligomer is selected from the group consisting of ethylene, propylene, n-butylene, isobutylene, isoprene, styrene, substituted styrene, conjugated dienes, e.g. 1,3-butadiene, acrolein, vinyl acetate, vinylpyrrolidone, vinylimidazole, maleic anhydride, (alkyl)acrylic acid anhydrides, (alkyl)acrylic acid salts, (alkyl)acrylic esters, (meth)acrylonitriles, (alkyl)acrylamides, vinyl halides and vinylidene halides.

Preferred ethylenically unsaturated monomers are ethylene, propylene, n-butylene, isobutylene, isoprene, 1,3-butadiene, α-C$_5$–C$_{18}$alkene, styrene, α-methyl- or p-methyl styrene, or a compound of the formula CH$_2$=C(R$_a$)—(C=Z)—R$_b$, wherein R$_a$ represents hydrogen or C$_1$–C$_4$alkyl;

R$_b$ represents NH$_2$, O$^-$(Me$^+$), glycidyl, C$_1$–C$_{18}$alkoxy, C$_2$–C$_{100}$alkoxy interrupted by at least one N and/or O atom, or hydroxy-substituted C$_1$–C$_{18}$alkoxy, C$_1$–C$_{18}$alkylamino, di(C$_1$–C$_{18}$alkyl)amino, hydroxy-substituted C$_1$–C$_{18}$alkylamino or hydroxy-substituted di(C$_1$–C$_{18}$alkyl) amino, —O—CH$_2$—CH$_2$—N(CH$_3$)$_2$ or —O—CH$_2$—CH$_2$—N$^+$H(CH$_3$)$_2$ An$^-$ with An$^-$ being the anion of a monovalent organic or inorganic acid; and Me being the anion of a monovalent metal atom or the ammonium ion; and Z represents oxygen or sulphur.

Examples for R$_a$ defined as C$_2$–C$_{100}$alkoxy interrupted by at least one O atom are illustrated by the partial formula:

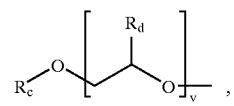

wherein

R$_c$ represents C$_1$–C$_{25}$alkyl, phenyl or phenyl substituted by C$_1$–C$_{18}$alkyl;

R$_d$ represents hydrogen or methyl; and v is a numeral from 1 to 50.

These monomers are for example derived from non-ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

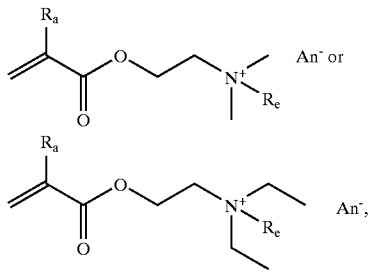

wherein An⁻ and $R_a$ have the meanings as defined above and $R_e$ represents methyl or benzyl. An⁻ represents preferably Cl⁻, Br⁻ or $CH_3SO_3^-$.

Further examples of suitable acrylate or methacrylate monomers are given below:

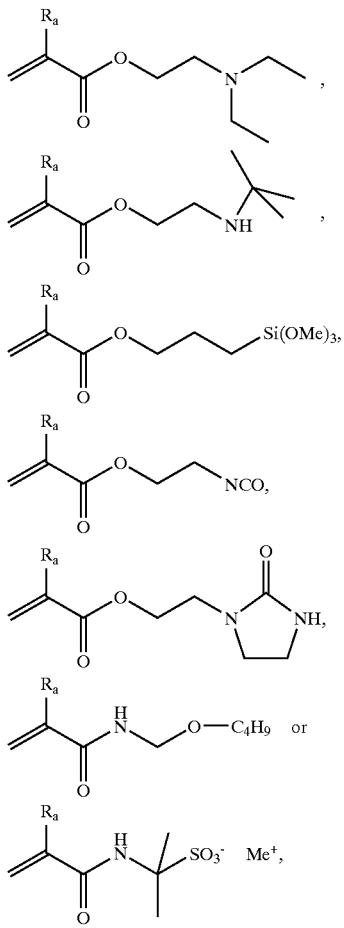

wherein $R_a$ has the meanings as defined above. Examples for suitable monomers other than acrylates are

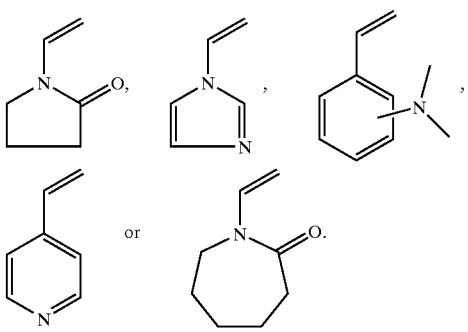

Preferably $R_a$ represents hydrogen or methyl, $R_b$ represents $NH_2$, glycidyl, $C_1$–$C_4$alkoxy, $C_1$–$C_4$alkoxy substituted or with hydroxy, $C_1$–$C_4$alkylamino; di($C_1$–$C_4$alkyl)amino, hydroxy-substituted $C_1$–$C_4$alkylamino or hydroxy-substituted di($C_1$–$C_4$alkyl)amino; and Z represents oxygen.

Particularly preferred ethylenically unsaturated monomers are styrene or methyl, ethyl, n-butyl, isobutyl, tert-butyl, 2-hydroxyethyl, 3-hydroxypropyl, 2-dimethylaminoethyl or glycidyl acrylates or methyl (meth)acrylate, ethyl (meth) acrylate, n-butyl (meth) acrylate, 2-hydroxyethyl (meth) acrylate, 3-hydroxypropyl (meth) acrylate, 2-dimethylaminoethyl (meth)acrylate, glycidyl (meth) acrylate, acrylonitrile, acrylamide, methacrylamide or 3-dimethylaminopropylmethacrylamide.

4. Definitions with Regard to the Radical Initiator

The polymerisation reaction may be carried out using the known methods of so-called photoinitiated radical polymerisation. The radical initiator (photoinitiator) employed in this method is of any known class. In certain cases it may be of advantage to use mixtures of at least two or photoinitiator. Typical classes of photoinitiator are, for example, camphor quinine, benzophenone, benzoenone derivatives, acetophenone, acetophenone derivatives, for example α-hydroxycycloalkyl phenyl ketones or 2-hydroxy-2-methyl-1-phenylpropanone, dialkoxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers and benzil ketals, e.g. dimethyl benzil ketal, phenylglyoxalic esters and derivatives thereof, dimeric phenylglyoxalic esters, peresters, e.g. benzophenone tetracarboxylic peresters as described for example in EP-A-126 541, monoacyl phosphine oxides, e.g. (2,4,6-trimethylbenzoyl) diphenylphosphine oxide, bisacylphosphine oxides, bis(2,6-dimethoxy-benzoyl)-(2,4,4-trimethyl-pentyl)phosphine oxide, bis(2,4,6-trimethylbenzoyl)-phenylphosphine oxid, bis(2,4,6-trimethylbenzoyl)-2,4-dipentoxyphenylphosphine oxide, trisacylphosphine oxides, halomethyltriazines, e.g. 2-(2-(4-methoxy-phenyl)-vinyl)-4,6-bis-trichloromethyl-(1, 3,5)triazine, 2-(4-methoxy-phenyl)-4,6-bis-trichloromethyl-(1,3,5)triazine, 2-(3,4-dimethoxy-phenyl)-4,6-bis-trichloromethyl-(1,3,5)triazine, 2-methyl-4,6-bis-trichloromethyl-(1,3,5)triazine, hexaarylbisimidazole/coinitiators systems, e.g. ortho-chlorohexaphenyl-bisimidazole combined with 2-mercaptobenz-thiazole, ferrocenium compounds, or titanocenes, e.g. bis(cyclopentadienyl)-bis(2,6-difluoro-3-pyrryl-phenyl) titanium.

The photopolymerisable compositions generally comprise 0.05 to 15.0% by weight, preferably 0.1 to 5.0% by weight, of the photoinitiator, based on the total weight of the composition. The amount refers to the total amount of the photoinitiators added, if mixtures of initiators are employed.

Preferred compounds are of the α-hydroxyketone type, phosphorus containing photoinitiators as well as the mixture of α-hydroxyketone compounds with phosphorous containing photoinitiators.

Preferred photoinitiators are of the formula PI

(PI)

wherein

Ar represents phenyl or phenyl substituted with a substituent selected from the group consisting of halogen, CN, OH, $C_1$–$C_{17}$alkoxy, phenoxy, $C_2$–$C_{12}$alkenyl, —S—$C_1$–$C_{12}$alkyl, —S-phenyl, —$SO_2$—$C_1$–$C_{12}$alkyl, —$SO_2$-phenyl, —$SO_2NH_2$, —$SO_2NH$—$C_1$–$C_{12}$alkyl, —$SO_2$—N($C_1$–$C_{12}$-alkyl)$_2$, —NH—$C_1$–$C_{12}$alkyl, —N($C_1$–$C_{12}$alkyl)$_2$, —NH—CO-phenyl, isocyanate and masked isocyanate, or represents phenyl, which is substituted with $C_1$–$C_{12}$alkyl or $C_1$–$C_{12}$alkyl which is substituted with a substituent selected from the group consisting of halogen, OH, CN, $NH_2$, COOH, isocyanate, masked isocyanate, alkenyl and masked alkenyl; or Ar represents thienyl, pyridyl, furyl, indanyl or tetrahydronaphthyl;

$R_{101}$ represents $C_1$–$C_8$alkyl or $C_1$–$C_8$alkyl, which is substituted with a substituent selected from the group consisting of OH, CN, $NH_2$, —NH$C_1$–$C_{12}$alkyl, —N($C_1$–$C_{12}$alkyl)$_2$, —NH—CO-phenyl, isocyanates, masked isocyanate, $C_2$–$C_{12}$alkenyl, halogen, $C_1$–$C_{12}$alkoxy, COOH, —(C=O)—O—$C_1$–$C_{12}$alkyl, —O—(C=O)—$C_1$–$C_8$alkyl and $NR_{103}R_{104}$, or $R_{101}$ represents $C_3$–$C_5$alkenyl, cyclopentyl, cyclohexyl or phenyl-$C_1$–$C_3$alkyl;

$R_{102}$ has one of the meanings given for $R_{101}$ or represents a group —$CH_2CH_2R_5$, or $R_{102}$ together with $R_{101}$ represent $C_2$–$C_8$alkylene, $C_3$–$C_9$oxaalkylene, $C_3$–$C_9$azaalkylene, or an exomethylene cyclohexane ring; with OH, CN, halogen, $C_1$–$C_{12}$alkoxy, —(C=O)—O—$C_1$–$C_{12}$alkyl, —O—(C=O)—$C_1$–$C_8$alkyl or $NR_{103}R_{104}$ being optional substituents of these groups;

$R_{103}$ represents $C_1$–$C_{12}$alkyl, or $C_2$–$C_4$alkyl substituted with OH, $C_1$–$C_8$alkoxy or CN, or $R_{103}$ represents $C_3$–$C_5$alkenyl, cyclohexyl, phenyl-$C_1$–$C_3$alkyl, phenyl or phenyl, which is substituted with Cl, $C_1$–$C_4$alkyl, OH, $C_1$–$C_4$alkoxy or —(C=O)—O—$C_1$–$C_8$alkyl;

$R_{104}$ represents $C_1$–$C_{12}$alkyl, $C_2$–$C_4$alkyl substituted with OH, $C_1$–$C_8$alkoxy or CN, or $R_{104}$ represents $C_3$–$C_5$alkenyl, cyclohexyl or phenyl-$C_1$–$C_3$alkyl, or $R_{104}$ together with $R_{103}$ represents $C_4$–$C_5$alkylene, which may be interrupted by —O— or —$NR_{105}$—, or $R_{104}$ together with $R_{102}$ represent $C_1$–$C_9$alkylene, $C_2$–$C_3$oxaalkylene or $C_2$–$C_3$azaalkylene; and $R_{105}$ represents $C_1$–$C_4$alkyl, —$CH_2CH_2CN$ or —$CH_2CH_2$(C=O)—O—$C_1$–$C_8$alkyl.

$C_1$–$C_{12}$alkyl is straight chained or branched if possible and is, for example, $C_1$–$C_{10}$, $C_1$–$C_8$ or preferable $C_1$–$C_6$alkyl, especially $C_1$–$C_4$alkyl. Representative examples include methyl, ethyl, propyl, isopropyl, n-butyl, sec-butyl, isobutyl, tert-butyl, pentyl, hexyl, heptyl, 2,4,4-trimethyl-pentyl, 2-ethylhexyl, octyl, nonyl, decyl, undecyl or dodecyl, preferably methyl or n-butyl.

$C_1$–$C_8$alkyl and $C_2$–$C_4$alkyl have the same meanings as given above with regard to the number of C-atoms as indicated.

$C_1$–$C_{17}$alkoxy is straight chained or branched if possible and is for example $C_1$–$C_{12}$, $C_1$–$C_8$ or preferably $C_1$–$C_6$alkoxy, especially $C_1$–$C_4$alkoxy. Examples are methoxy, ethoxy, n-propoxy, isopropoxy, n-butoxy, sec-butoxy, iso-butoxy, tert-butoxy, pentyloxy, hexyloxy, heptyloxy, 2,4,4-trimethylpentyloxy, 2-ethylhexyloxy, n-octyloxy, nonyloxy, decyloxy, dodecyloxy, tetradecyloxy, pentadecyloxy, hexadecyloxy or heptadecyloxy, especially methoxy, ethoxy, n-propoxy, isopropoxy, n-butoxy, sec-butoxy, iso-butoxy, tert-butoxy, most preferably methoxy.

$C_1$–$C_{12}$alkoxy, $C_1$–$C_8$alkoxy and $C_1$–$C_4$alkoxy have the same meanings as given above with regard to the number of C-atoms as indicated.

$C_2$–$C_{12}$alkenyl has at least one double bond and is for example $C_2$–$C_8$, $C_2$–$C_6$ or $C_3$–$C_5$alkenyl, especially $C_2$–$C_4$-alkenyl. Examples are allyl, methallyl, 1,1-dimethylallyl, 1-butenyl, 3-butenyl, 2-butenyl, 1,3-pentadienyl, 5-hexenyl, 7-octenyl, nonenyl, dodecenyl, especially allyl.

$C_3$–$C_5$alkenyl has the same meanings as given above with regard to the number of C-atoms as indicated.

In the groups —S—$C_1$–$C_{12}$alkyl, —$SO_2$—$C_1$–$C_{12}$alkyl, —C(=O)O—$C_1$–$C_{12}$alkyl, —$SO_2NH$—$C_1$–$C_{12}$alkyl, —$SO_2N(C_1$–$C_{12}$-alkyl)$_2$, —NH—$C_1$–$C_{12}$alkyl and —N($C_1$–$C_{12}$alkyl)$_2$ $C_1$–$C_{12}$alkyl has the meanings given above. In the groups —O—(C=O)—$C_1$–$C_8$alkyl, —C(=O)—NH—$C_1$–$C_8$alkyl, —C(=O)—N($C_1$–$C_8$alkyl)$_2$, —$CH_2CH_2$(C=O)O—$C_1$–$C_8$alkyl and —P(=O)(O—$C_1$–$C_8$alkyl)$_2$ $C_1$–$C_8$alkyl has the same meanings as given above.

If $C_1$–$C_{12}$alkyl is substituted with halogen, up to three halogen substituents are located at the alkyl.

The term "masked isocyanate" defines a protected isocyanate group, namely an isocyanate group, which is blocked by chemical groups that can be removed under specific reaction conditions. To give an illustrative example, the formation of an oxime results in a masked isocyanate group, cf. *J. Coatings Technology*, Vol. 61, No. 775 (August 1989). The blocking/deblocking mechanism is, for example, demonstrated by the following equation:

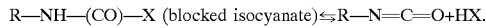

R—NH—(CO)—X (blocked isocyanate)⇌R—N=C=O+HX.

The blocking has the effect that the protected isocyanates group remains inert to reactions performed with the composition and low temperature reaction conditions. Under the influence of temperature (>120° C.) HX is removed with subsequent liberation of the isocyanate group, which is then capable of taking part in further reactions, for example with cross linkers. Suitable blocking agents HX are, for example, phenol, caprolactam, methyl ethyl ketoxime and diethyl malonate.

Phenyl-$C_1$–$C_3$alkyl is, for example, benzyl, 1- or 2-phenylethyl or 1- or 2-phenylpropyl, especially benzyl.

$C_2$–$C_8$alkylene is straight chained or branched if possible, and is, for example, methylene, ethylene, 1,3-propylene, 1-methylethylene, 1,1-dimethylethylene, 1,4-butylene, 1-methylpropylene, 2-methylpropylene, pentylene, hexylene, heptylene or octylene, especially hexylene.

$C_4$–$C_5$alkylene, which may be interrupted by —O— or —$NR_{105}$—, is, for example,

—$CH_2CH_2$—O—$CH_2CH_2$—,

—$CH_2CH_2$—($NR_{105}$)—$CH_2CH_2$—,

—$CH_2$—O—$CH_2CH_2CH_2$—,

—CH$_2$—(NR$_{105}$)—CH$_2$CH$_2$CH$_2$— or

—CH$_2$CH$_2$—O—CH$_2$CH$_2$CH$_2$—.

C$_3$–C$_9$oxaalkylene may contain, for example, 1, 2 or 1–3 O-atoms, especially 1 O-atom and is, for example, —CH$_2$—O—CH$_2$—, —CH$_2$CH$_2$O—CH$_2$CH$_2$—; —CH$_2$—CH(CH$_3$)—O—CH$_2$CH$_2$— or —[CH$_2$CH$_2$O]$_y$, wherein y=1–4.

C$_3$–C$_9$azaalkylene may contain, for example, 1, 2 or 1–3 (NR$_{105}$)-groups, especially 1 such group and is, for example, —CH$_2$—(NR$_{105}$)—CH$_2$—, —CH$_2$CH$_2$—(NR$_{105}$)—CH$_2$CH$_2$—, —CH$_2$—CH(CH$_3$)—(NR$_{105}$)—CH$_2$CH$_2$CH$_2$— or —[CH$_2$CH$_2$(NR$_{105}$)]$_y$, wherein y=1–4 and R$_{105}$ has the meanings given above.

The exomethylene cyclohexane ring has the following structure

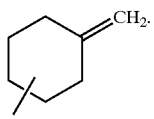

Halogen is fluorine, chlorine, bromine and iodine, especially chlorine and bromine, preferably chlorine.

Preferably Ar in the formula Pi is phenyl or phenyl substituted by C$_1$–C$_{12}$alkyl or phenyl substituted by hydroxy-C$_1$–C$_4$alkyl.

R$_{101}$ and R$_{102}$ are C$_1$–C$_4$alkyl, or R$_{102}$ together with R$_{101}$ and the C-atom to which they are bonded, are C$_2$–C$_8$alkylene.

Suitable compounds of the formula PI are selected from the group consisting of phenyl-1-hydroxycyclohexylketone (®Irgacure 184; Ciba Specialty Chemicals); 4-dodecylphenyl-2-hydroxy-prop-2-yl ketone; 4-isopropylphenyl-2-hydroxy-prop-2-yl ketone; 2-hydroxy-2-methyl-1-phenyl-propanone; [4-(2-hydroxyethyl)-phenyl]-2-hydroxy-prop-2-yl ketone; 4-methylphenyl-2-hydroxy-prop-2-yl ketone; and [4-(2-carboxyethyl)-phenyl]-2-hydroxy-prop-2-yl ketone.

Especially preferred are phenyl-1-hydroxycyclohexylketone, 2-hydroxy-2-methyl-1-phenyl-propanone, [4-(2-hydroxyethyl)-phenyl]-2-hydroxy-prop-2-yl ketone and [4-(2-carboxy-ethyl)phenyl]-2-hydroxy-prop-2-yl ketone.

The photoinitators according to the formula PI are known, some of the compounds are commercially available or obtainable by synthetic methods known in the art. The compounds and their preparation are, for example, disclosed in U.S. Pat. Nos. 4,308,400; 4,315,807; 4,318,791; 4,721,734; 4,347,111; 4,477,681; 4,861,916; 5,045,573.

Preferred is also a mixture of photoinitiators of at least one compound of the formula PI and at least one phosphorus containing photoinitiator of the formulae PIIa or PIIb

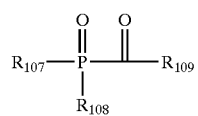 (PIIa)

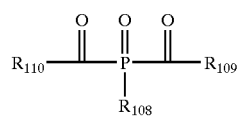 (PIIb)

wherein

R$_{107}$ and R$_{108}$ independently of one another represent C$_1$–C$_{18}$alkyl, cyclohexyl, cyclopentyl, phenyl, naphthyl or biphenyl, or cyclohexyl, cyclopentyl, phenyl, naphthyl or biphenyl substituted with halogen, C$_1$–C$_{12}$alkyl and/or C$_1$–C$_{12}$alkoxy; or R$_{107}$ and R$_{108}$ form a 5- or 6-membered S- or N-containing heterocyclic ring; or R$_{107}$ and R$_{108}$ together with the P-atom to which they are bonded form a ring, which contains from 4 to 10 carbon atoms and which ring may be substituted by 1 to 6 C$_1$–C$_4$alkyl radicals.

R$_{109}$ and R$_{110}$ independently of one another represent cyclohexyl, cyclopentyl, phenyl, naphthyl or biphenyl, or cyclohexyl, cyclopentyl, phenyl, naphthyl or biphenyl substituted by halogen, C$_1$–C$_4$alkyl and/or C$_1$–C$_4$alkoxy; or R$_{109}$ and R$_{110}$ form a 5- or 6-membered S- or N-containing heterocyclic ring, C$_1$–C$_{18}$Alkyl is straight chained or branched or branched if possible and is, for example, C$_1$–C$_{12}$-, C$_1$–C$_{10}$-, C$_1$–C$_8$- or C$_1$–C$_6$-alkyl, especially C$_1$–C$_4$alkyl. Examples are methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl or octadecyl.

C$_1$–C$_{12}$alkyl has the same meanings as given above with regard to the number of C-atoms as indicated.

Preferably R$_{108}$ defined as C$_1$–C$_{18}$alkyl is C$_4$–C$_8$alkyl, for example n-butyl, tert-butyl, isobutyl, sec-butyl, n-octyl, 2,4,4-trimethylpentyl.

C$_1$–C$_{12}$alkoxy is straight chained or linear if possible and is, for example, C$_1$–C$_8$- or C$_1$–C$_6$alkoxy, especially C$_1$–C$_4$alkoxy. Representative examples include methoxy, ethoxy, propoxy, isopropoxy, n-butoxy, sec-butoxy, isobutoxy, tert-butoxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butoxy, sec-butoxy, isobutoxy, tert-butoxy, preferably methoxy.

Halogen is fluorine, chlorine, bromine and iodine, especially chlorine and bromine, preferably chlorine.

Naphthyl means α- or β-naphthyl.

Substituted cyclopentyl, cyclohexyl, phenyl, naphthyl or biphenyl groups have at least one and up to five substituents. For substituted phenyl the substitution in the 4-, 2,5-, 2-, 2,6- or 2,4,6-positions is preferred. Representative Examples include 4-chlorophenyl, 2,6-dichlorophenyl, 2,4,6-trichlorophenyl, 2,6-difluorophenyl, 2-or 4-tolyl, 2- or 4-ethylphenyl, 4-tert-butylphenyl, 4-dodecylphenyl, 2- or 4-methoxyphenyl, 2,6-dimethoxyphenyl, 4-hexyloxyphenyl, 2,4-dimethylphenyl, 2,4,6-trimethylphenyl, 1- or 2-methylnaphthyl, 1- or 2-isopropyinaphthyl, 1- or 2-chloronaphthyl or 1- or 2-ethoxynaphthyl. Other groups are, for example, 4-methoxy-2-ethylphenyl or 4-ethoxy-2-methylphenyl.

R$_{109}$ and R$_{110}$ preferably are substituted phenyl, for example 2,6-dimethoxyphenyl, 2,6-dichlorophenyl, 2,4,6-trimethylphenyl, especially 2,4,6-trimethylphenyl.

A 5- or 6-membered S- or N-containing heterocyclic ring is, for example, thienyl, pyrryl, pyrazolyl, thiazolyl, pyridyl or 1,3-, 1,2- or 1,4-diazyl, preferably thienyl or pyrryl.

If R$_{107}$ and R$_{108}$ together with the P-atom to which they are bonded form a ring containing 4 to 10 C-atoms this ring is monocyclic, bicyclic or tricyclic. A monocyclic ring formed together with the P-atom is preferably a phosphacyclopentane ring. A bicyclic ring formed together with the P-atom is preferably a phosphabicyclohexane or phosphabicyclononane ring. A tricyclic ring formed together with the P atom is preferably a (6H)-dibenzo[c,e][1,2]-oxaphosphorine ring.

$R_{109}$ and $R_{110}$ are preferably 2,6-dimethoxyphenyl, 2,6-dimethylphenyl, 2,6-dichlorophenyl or especially 2,4,6-trimethylphenyl.

$R_{107}$ and $R_{108}$ preferably are $C_1$–$C_{18}$alkyl, cyclohexyl, cyclopentyl, phenyl or phenyl substituted with $C_1$–$C_4$alkyl. Specifically preferred $R_{107}$ and $R_{108}$ are n-butyl, tert-butyl, isobutyl, sec-butyl, n-octyl, 2,4,4-trimethylpentyl, phenyl or 2,5-dimethylphenyl.

The photoinitators according to the formulae PIIa and PIIb are known, some are commercially available or obtainable by synthetic methods known in the art. They are, for example, disclosed in U.S. Pat. Nos. 4,792,632; 4,737,593; 4,298,738; 5,218,009; 5,399,770; 5,472,992.

Suitable compounds of the formula PIIa and PIIb are 2,4,6-Trimethylbenzoyl-diphenyl-phosphine oxide;
bis(2,4,6-Trimethylbenzoyl)-2,4-di(3-methyl-but-1-oxy) phenyl-phosphine oxide;
bis(2,4,6-Trimethylbenzoyl)-2,4-dipentyloxyphenyl-phosphine oxide;
bis(2,4,6-Trimethylbenzoyl)-2-methylprop-1-yl-phosphine oxide;
bis(2,6-Dimethoxybenzoyl)-2,4,4-trimethylpent-1-yl-phosphine oxide;
bis(2,4,6-Trimethylbenzoyl)-phenyl phosphine oxide;

Representative Examples for photoinitiator mixtures are mixtures of:

bis(2,6-Dimethoxybenzoyl)-2,4,4-trimethylpent-1-yl-phosphine oxide with 2-hydroxy-2-methyl-1-phenyl-propanone;
2-Hydroxy-2-methyl-1-phenyl-propanone with (2,4,6-trimethylbenzoyl)-diphenyl phosphine oxide;
Phenyl-1-hydroxycyclohexylketone with bis(2,6-dimethoxybenzoyl)-2,4,4-trimethylpent-1-yl-phosphine oxide;
Phenyl-1-hydroxycyclohexylketone with bis(2,4,6-trimethylbenzoyl)-2-methyl-prop-1-yl-phosphine oxide;
Phenyl-1-hydroxycyclohexylketone with bis(2,4,6-trimethylbenzoyl)-phenyl phosphine oxide;
Phenyl-1-hydroxycyclohexylketone with bis(2,4,6-trimethylbenzoyl)-2,4-dipentyloxyphenyl-phosphine oxide;
2-Hydroxy-2-methyl-1-phenyl-propanone with bis(2,4,6-trimethylbenzoyl)-2-methyl-prop-1-yl-phosphine oxide;
2-Hydroxy-2-methyl-1-phenyl-propanone with bis(2,4,6-trimethylbenzoyl)-phenyl phosphine oxide; and
2-Hydroxy-2-methyl-1-phenyl-propanone with bis(2,4,6-trimethylbenzoyl)-2,4-dipentyloxy-phenyl-phosphine oxide.

The amount of the photoinitiator compounds of the formula PI in the mixtures of these compounds with phosphorus containing photoinitiators compounds of the formula PIIa or PIIb is, for example, 50.0–95.0% by weight. Preferably the amount of the compounds of the formula PI in the mixture is 50.0–75.0%, especially 75.0% (based on 100% by weight of the total mixture).

Of particular interest is a process, wherein a photoinitiator of the formula PI is employed and wherein Ar represents phenyl or phenyl substituted by $C_1$–$C_{12}$alkyl or $C_1$–$C_{12}$alkyl which in turn is substituted by OH or COOH, and wherein $R_{101}$ and $R_{102}$ represent $C_1$–$C_{18}$alkyl or $R_{101}$ together with $R_{102}$ represent $C_2$–$C_8$alkylene, and wherein a photoinitiator of the formula PIIa or the formula PIIb is employed and wherein $R_{107}$ and $R_{108}$ independently of one another represent $C_1$–$C_{12}$alky, phenyl or phenyl by $C_1$–$C_8$alkyl and/or $C_1$–$C_8$alkoxy and wherein $R_{109}$ and $R_{110}$ independently of one another represent phenyl, which is substituted by halogen, $C_1$–$C_4$alkyl and/or $C_1$–$C_4$alkoxy.

Preferred is, for example, a mixture of 2-hydroxy-2-methyl-1-phenyl-propanone with bis(2,6-dimethoxybenzoyl)-2,4,4-trimethylpent-1-yl-phosphine oxide. Especially preferred is the above mixture with an amount of 2-hydroxy-2-methyl-1-phenyl-propanone of 75.0% by weight.

Also preferred, for example, is a mixture of 2-hydroxy-2-methyl-1-phenyl-propanone with 2,4,6-trimethylbenzoyl-phenyl-phosphine oxide. Especially preferred is the above mixture with an amount of 2-hydroxy-2-methyl-1-phenyl-propanone of 50.0% by weight.

The composition to be (co) polymerised in the instant process may contain the photoinitiators of the formulae PI, PIIa or PIIb, or mixtures thereof in an amount from about 0.1 to 15.0% by weight, preferably from about 0.2 to 5.0% by weight, based on the total solids content.

Additional coinitiators or sensitisers may be used in the process. These are typically dyes that react by energy transfer or electron transfer and enhance the overall quantum yield. Suitable dyes are for example dyes with triarylmethane structure, such as malachite green, indoline, thiazine, such as methylene blue, xanthone, thioxanthone, oxazine, acridine or phenazine, such as safranine, or rhodamine of the formula

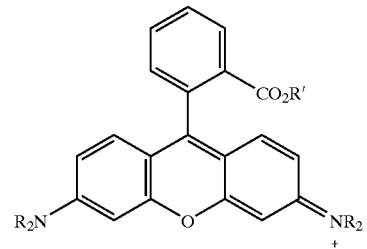

wherein R represents alkyl or aryl and R' represents hydrogen, alkyl or aryl. Examples are Rhodamin B, Rhodamin 6G or Violamin R, Sulphorhodamin B or Sulphorhodamin G.

Preferred are thioxanthone, oxazine, acridine, phenazine or rhodamine.

The polymerisation reaction may also be carried out using thermally initiated radical polymerisation. The source of radicals may be a bis-azo compound, a peroxide or a hydroperoxide.

Most preferably, the source of radicals is 2,2'-azobisisobutyronitrile, 2,2'-azobis(2-methyl-butyronitrile), 2,2'-azobis(2,4-dimethylvaleronitrile), 2,2'-azobis(4-methoxy-2,4-dimethyl-valeronitrile), 1,1'-azobis(1-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis(2-methyl-N-[1,1-bis (hydroxymethyl)ethyl]propionamide) or 2,2'-azobis(2-methyl-N-[1,1-bis(hydroxymethyl)-2-hydroxyethyl] propionamide.

Preferred peroxides and hydroperoxides are acetyl cyclohexane sulphonyl peroxide, diisopropyl peroxy dicarbonate, t-amyl perneodecanoate, t-butyl perneodecanoate, t-butyl perpivalate, t-amylperpivalate, bis(2,4-dichlorobenzoyl) peroxide, diisononanoyl peroxide, didecanoyl peroxide, dioctanoyl, peroxide, dilauroyl peroxide, bis (2-methylbenzoyl) peroxide, disuccinic acid peroxide, diacetyl peroxide, dibenzoyl peroxide, t-butyl per-2-ethylhexanoate, bis-(4-chlorobenzoyl)-peroxide, t-butyl perisobutyrate, t-butyl permaleinate, 1,1-bis(t-butylperoxy) 3,5,5-trimethylcyclohexane, 1,1-bis(t-butylperoxy) cyclohexane, t-butyl peroxy isopropyl carbonate, t-butyl perisononaoate, 2,5-dimethylhexane 2,5-dibenzoate, t-butyl peracetate, t-amyl perbenzoate, t-butyl perbenzoate, 2,2-bis (t-butylperoxy) butane, 2,2 bis (t-butylperoxy) propane, dicumyl peroxide, 2,5-dimethylhexane-2,5-di-t-butylperoxide, 3-t-butylperoxy 3-phenylphthalide, di-t-amyl peroxide, α, α'-bis(t-butylperoxy isopropyl) benzene, 3,5-bis (t-butylperoxy)3,5-dimethyl 1,2-dioxolane, di-t-butyl peroxide, 2,5-dimethylhexyne-2,5-di-t-butylperoxide, 3,3,6, 6,9,9-hexamethyl 1,2,4,5-tetraoxacyclononane, p-menthane hydroperoxide, pinane hydroperoxide, diisopropylbenzene mono-α-hydro-peroxide, cumene hydroperoxide or t-butyl hydroperoxide.

These compounds are commercially available.

Another subject of the present invention is a process for preparing an acid oligomer, an acid cooligomer, an acid polymer or an acid copolymer (block or random) by free radical polymerisation of a) an acid monomer or oligomer of acrylic acid or of an acid derivative of acrylic acid or mixtures thereof, or of a mixture of an ethylenically unsaturated monomer or oligomer and an acid monomer or oligomer selected from acrylic acid or of an acid derivative of acrylic acid;

which comprises (co)polymerising the monomers or oligomers in the presence of b) a radical initiator which forms a radical upon heating or upon irradiation with (UV) light from 305 nm to 450 nm, and c) a compound of the formulae (Ia), (Ib) or (Ic) as defined above, by subjecting the mixture to heat or electromagnetic radiation with a wavelength of the range from 305 nm to 450 nm. Definitions and preferences for the different components of the compositions and their substituents have been mentioned above and apply for the polymerisation process, too.

The compound of the formulae (Ia), (Ib) or (Ic) is present in an amount of about 0.01 to 20.0 weight %, based on the weight of the monomer or monomer mixture. The radical initiator b) is present in an amount of about 0.01 to 5.0 weight %, based on the weight of the monomer or monomer mixture. The ratio of radical initiators to the compounds of the formulae (Ia), (Ib) or (Ic) is preferably about 0.1 to 10.0, more preferably about 0.1 to 5.0 and most preferably about 0.1 to 1.0.

The process can be carried out in aqueous solutions. Aqueous polymerisation reactions can be supplemented with a water-miscible or hydrophilic co solvent to ensure that the reaction mixture remains homogeneous in a single phase throughout the monomer conversion. Any water-soluble or water-miscible co solvent may be used, as long as the aqueous solvent medium is effective in providing a solvent system that prevents precipitation or phase separation of the reactants or polymer products until completion of the polymerisation reactions. Exemplary co solvents useful in the process may be selected from the group consisting of aliphatic alcohols, glycols, glycol ethers, pyrrolidines, N-alkyl pyrrolidinones, N-alkyl pyrrolidones, polyethylene glycols, polypropylene glycols, amides, carboxylic acids and salts thereof, esters, organosulphides, sulphoxides, sulphones, alcohol derivatives, hydroxyether derivatives, such as butyl carbitol or cellosolve, amino alcohols, and ketones, and the like, as well as derivatives thereof and mixtures thereof. Specific examples include methanol, ethanol, propanol, dioxane, ethylene glycol, propylene glycol, diethylene glycol, glycerol, dipropylene glycol, and other water-soluble or water-miscible solvents, and mixtures thereof. When mixtures of water and water-soluble or water-miscible organic liquids are selected as the aqueous reaction media, the water to co solvent weight ratio is typically in the range from about 100:0 to about 10:90.

The process may also be carried out in the presence of an organic solvent. Additional cosolvents or surfactants, such as glycols or ammonium salts of fatty acids, may then be present.

If organic solvents are used solvents of medium polarity are preferred, such as halogenated hydrocarbons, e.g. chlorobenzene, alkanols, e.g. methanol, ethanol, ethylene glycol, or ethylene glycol monomethyl ether, esters, e.g. ethyl acetate, propyl, butyl or hexyl acetate or glycol ethers, e.g. ethylene glycol dimethyl ether, or mixtures thereof.

Preferred processes use as little solvents as possible. In the reaction mixture it is preferred to use more than 30.0% by weight of monomer and initiator, particularly preferably more than 50.0%.

The process can be initiated thermally or photochemically. The thermally initiated reaction may be carried out in any vessel suitable for radical polymerisation reactions. Examples are known in the art.

Preferably the reaction temperature is kept between 40° and 120° C. The time length for the reaction time may vary, depending on the molecular weight desired. Typical reaction lengths range from 1 to 24 hours.

The photochemically initiated radical polymerisation may be carried out, for example, in an apparatus as described in WO 98/371 05.

The reaction vessel used to prepare the compounds according to the Examples consists of Rodoxal®, an aluminium alloy, but other suitable reactors that consist of alternative materials may also be used, for example stainless steel or any material compatible with the monomers employed, for example teflon, brown glass etc.. The reactor possesses a glass window allowing transmission of the UV-light. The overall irradiation surface of the reactor is about 26 $cm^2$ and the cell thickness is about 1 cm. The term "overall irradiation surface" of the reactor means the surface of the irradiated part of the reactor, namely the window. The term "cell thickness" defines the thickness of the internal path (diameter) of the reactor at the irradiated part. The process can also be carried out using an optical bench and a UV-cell for absorption spectra equipped with a magnetic stirrer and fitted with a septum to allow reactions under argon. This UV-cell, similar to those used to measure UV-spectra, may be irradiated through a 2 $cm^2$ window with homogeneous light source from a Philips 100 W medium pressure mercury lamp. The cooling may be effected through the side walls of the cell.

Larger reactor dimensions, such as an overall irradiation surface (window size) of 26 $cm^2$ with a cell thickness (diameter) of 1 cm, require need light sources of higher intensity and larger irradiation surfaces, such as Fusion Curing lamps F200 to F600. As those commercially available lamps have a bulb length of 6 inches (about 15.5 cm; F200 lamp) or 10 inches (about 25 cm; F600 lamp), the reactor vessel should not exceed this height. The irradiation surface can thus be adapted to the necessary reaction conditions. To obtain a controllable and homogeneous generation of radicals of the photoinitiator throughout the reactor, the flow of the mixture and the distribution of radicals in the mixture are controlled by stirring and appropriate irradiation. This is not dependent on the size of the reactor or the irradiation surface.

The time length for the reaction depends on the intensity of the UV-lamp, the area of irradiation, monomer and initiator concentration and may thus vary in a very wide range, depending on the conditions used.

The reaction temperature of the photochemically induced polymerisation is preferably kept between 20° and 70° C. The time length is preferably from 5 minutes to 5 h, more preferably from 10 minutes to 2 hours.

The above process can be conducted with high efficiency and yield. Due to their amphiphilic character the addition fragmentation agents (AFA),of the formulae (Ia), (Ib) and (Ic) are particularly suitable for the preparation of acid macromonomers based on (meth) acrylic acid.

The term macromonomers comprises acid oligomers, acid co-oligomers, acid polymers and acid copolymers comprises that contain at least one ethylenically unsaturated group and may be polymerised further in a subsequent polymerisation step, e.g. by photoinduced polymerisation.

AFA are soluble enough for the polymerisation process carried out in aqueous medium. Traces of non-reacted AFA can be removed after the polymerisation from the macromonomer product by simple extraction with a solvent of medium polarity. A further advantage is the fact that the process consists of one step and results in colourless products.

New Acid Macromonomers

The new acid macromonomers prepared according to process of above may be illustrated by the following formulae:

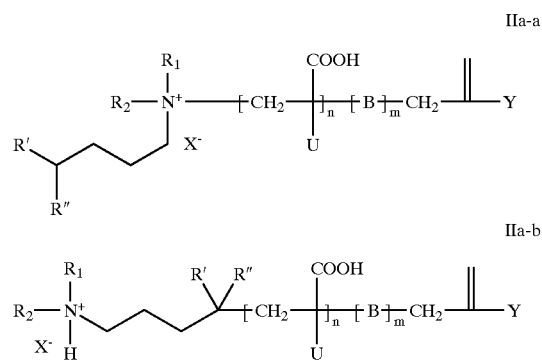

wherein $X^-$ and Y are as defined under the formulae (Ia), (Ib), (Ic);
$R_1$, $R_2$, $R_3$ are as defined under the formulae (Ia), (Ib), (Ic);
R represents the direct bond or linear or branched $C_1$–$C_5$alkylene; with the proviso that when R is $C_1$–$C_5$alkylene, one of the residues $R_1$, $R_2$ or $R_3$ is hydrogen;
U represents hydrogen, methyl, trifluoromethyl, carboxymethyl, methoxycarbonylmethyl, ethoxycarbonylmethyl, trifluoroethoxycarbonylmethyl, isopropoxycarbonylmethyl, hexafluoroisopropoxycarbonylmethyl, n-butoxycarbonylmethyl, n-dodecyloxycarbonylmethyl, 2-ethylhexoxycarbonylmethyl, perfluorooctyl-oxycarbonylmethyl, 1,2-dicarboxyeth-1-yl, benzyl or 4-benzyloxy-3-methoxyphenyl;
B represents a residue derived from the ethylenically unsaturated comonomer;
$m \geq 20$;
$n > 0$;

and when either or both of m and n are greater than 0, the repeat units are identical or different.

Thus, a further object of the present invention relates a polymer or copolymer prepared by the above process containing a vinyl- or 1,3-dienyl group as terminal group of the molecule.

Preferred are homo-oligomers or polymers, wherein m=0. are compounds of the formula IIa. With regard to the compounds of the formula IIa, especially preferred are those of the formulae IIa-a and IIa-b,

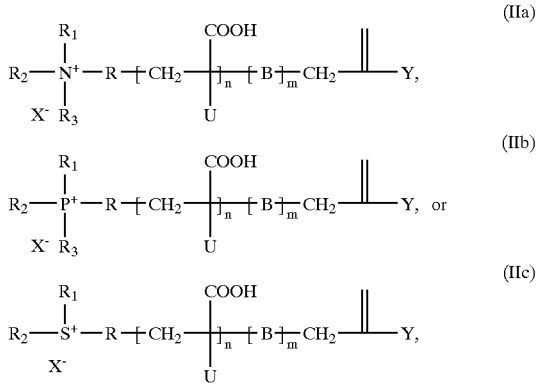

wherein $R_1$, $R_2$, U, B, $X^-$, Y, m and n are as defined above; and

R' and R" each independently of one another represent $C_1$–$C_{18}$alkyl, $C_3$–$C_{18}$alkyl interrupted by at least one nitrogen or oxygen atom, $C_3$–$C_{18}$alkenyl, $C_3$–$C_{18}$alkynyl or $C_7$–$C_9$phenylalkyl; or
$C_1$–$C_{18}$alkyl, $C_3$–$C_{18}$alkyl interrupted by at least one nitrogen or oxygen atom, $C_3$–$C_{18}$alkenyl, $C_3$–$C_{18}$alkynyl or $C_7$–$C_9$phenylalkyl, which are substituted with a substituent selected from the group consisting of $NO_2$, halogen, amino, hydroxy, cyano, carboxy, $C_1$–$C_4$alkoxy, $C_1$–$C_4$alkylthio, $C_1$–$C_4$alkylamino, di($C_1$–$C_4$alkyl)amino and the group —O—C(=O)—$C_1$–$C_{18}$alkyl.

Preferably the polymers have an average number molecular weight ($M_n$) of 1000–500 000, more preferably 5 000–300 000, and most preferably 5 000–100 000.

The polydispersity (PD) as defined by $M_n/M_w$ is preferably below 3, more preferably from 1.1 to 2.5, and most preferably from 1.1 to 2.

The chain transfer coefficient C is preferably from 0.4 to 1, more preferably from 0.6 to 1, and most preferably from 0.7 to 1.

The Use of the Acid Macromonomers

The acid oligomers/polymers prepared by the instant process and illustrated by the formulae IIa, IIb and IIc can be used to prepare structured polymers, such as block copolymers or graft/comb copolymers, for a wide range of industrial applications. These applications include their use as dispersants for solid particles in aqueous solutions, as stabilisers for latex preparations, as compatibilisers for polymer blends and the like. The structured polymers can also be used as binders in coatings, for example in an aqueous photopolymer coating that cannot easily be obtained with a linear polymer. Furthermore, the structured polymers can be used, for example, for the production of printing inks, varnishes, white paints, coating compositions, inter alia for paper, wood, metal or plastic, for the production of coloured pigmented paints, daylight-curable coatings for buildings and road markings, for the preparation of clear or pigmented aqueous dispersions, for the production of printing plates, for the production of masks for screen printing, as dental filling materials, for the production of adhesives, of etch or permanent resists and of solder stop masks for printed electronic circuits, for the production of three-dimensional articles by bulk curing (UV curing in transparent moulds) or for the production of formulations used in the stereo lithography process, as described, for example, in U.S. Pat. No. 4,575,330, for the preparation of composite materials (for example styrenic polyesters, which may contain glass fibres and other assistants) and other thick-layer compositions, for the production of coatings for encapsulation of electronic parts or for the production of coatings for optical fibres.

New Addition Fragmentation Agents

Compounds of the formulae (Ia), (Ib) and (Ic) wherein Y represents —S(=O)$R_8$, —S(=O)$_2R_9$, —P(=O)$R_{10}R_{11}$, —P(=O)(O$R_{12}$)$_2$ or —P(=O)(N$R_{13}R_{14}$)$_2$ are new.

Thus, a further subject of the present invention are compounds of the formulae (Ia), (Ib) or (Ic) wherein, Y represents —S(=O)$R_8$, —S(=O)$_2R_9$, —P(=O)$R_{10}R_{11}$, —P(=O)(O$R_{12}$)$_2$ or —P(=O)(N$R_{13}R_{14}$)$_2$ with $R_8$, $R_9$, $R_{10}$, $R_{11}$, $R_{12}$, $R_{13}$ $R_{14}$ as defined above; and $R_1$, $R_2$, $R_3$, $X^-$ and n are as defined above.

New Addition Fragmentation Agents Selected from those Generically Disclosed in WO 00/11041

Compounds of the formula (Ia), wherein $X^-$ represents an anionic group derived from an aromatic sulphonic acid surprisingly control the molecular weight build up and the polymerisation process with better efficiency and yield.

Thus, the new compounds of the formula (Ia) are a further object of the invention, wherein $R_1$, $R_2$, $R_3$, Y and n are as defined above and $X^-$ represents the anion of benzenesulphonic acid or 1- or 2-naphthalenesulphonic acid or 1- or 2-naphthalenesulphonic acid which is substituted by one or two radicals selected from the group consisting of $C_1$–$C_{12}$ alkyl, $C_1$–$C_{12}$ alkoxy, $C_1$–$C_{12}$alkylthio, halogen, nitro, hydroxy, carboxy, $C_1$–$C_4$alkylamino and di($C_1$–$C_4$alkyl) amino; with the proviso that when $X^-$ represents the anion of p-toluenesulphonic acid, the cationic radical —$N^+R_1R_2R_3$ is other than the dioctylmethyl ammonium radical.

The compounds of the formulae (Ia), (Ib), (Ic) can be prepared according to known methods.

An analogous synthesis is for example described in U.S. Pat. No. 4,247,700 as well as in CA96: 163229c. The synthesis of the acrylic and acrylonitrile derivatives is carried out by Mannich reaction of the aliphatic amine with cyanoacetic acid or monoesters of malonic acid in the presence of formaldehyde solutions in water, followed by reaction with an alkylating agent. The styrene equivalent is synthesised in analogy to W 88/04304 starting from α-bromomethyl styrene and the corresponding amine. Another possibility is described by in Melikyan et al. in *Chemistry Papers* 46 (4), 269–271 (1992) starting from the corresponding cinnamates.

The synthesis of the following compounds is described in WO 00/11041. Preferred compounds of the formula Ia wherein Y is phenyl, n is 0 are:

| $R_1$ | $R_2$ | $R_3$ | $X^-$ |
|---|---|---|---|
| hydrogen | hydrogen | n-octyl | $Br^-$ or $BF_4^-$ |
| hydrogen | n-octyl | n-octyl | $BF_4^-$ or $PF_4^-$ |
| Methyl | methyl | methyl | $Br^-$ or $BF_4^-$ |
| Methyl | methyl | ethyl | $Br^-$ |
| Methyl | methyl | n-butyl | $PF_6^-$ |
| Methyl | methyl | isobutyl | $Br^-$ |
| Methyl | methyl | n-octyl | $Br^-$, $CF_3SO_3^-$ or the anion of benzene sulphonic, p-toluenesulphonic or dimethylbenzene sulphonic acid |
| Methyl | methyl | but-3-enyl | $Br^-$ |
| Methyl | methyl | pent-4-enyl | $Br^-$ |
| Methyl | methyl | hex-4-enyl | $Br^-$ |
| Methyl | methyl | hydroxyethyl | $Br^-$ |
| Methyl | methyl | 2-(n-hexylcarbonyl-oxy)-pent-1-yl | $Br^-$ |
| Methyl | n-octyl | n-octyl | $Br^-$, $BF_4^-$, $B(Ph)_4^-$, $PF_6^-$ or $CF_3COO^-$ or the anion of dimethylbenzene-sulphonic acid |
| n-butyl | n-butyl | 2-butyl | $PF_4^-$ |
| n-hexyl | n-hexyl | 2-phenyleth-1-yl | $Br^-$ |
| Iso-pentyl | isopentyl | isopentyl | $Br^-$ |
| Iso-pentyl | n-octyl | n-octyl | $Br^-$ |
| n-octyl | n-octyl | n-octyl | $Br^-$ |
| together form a piperidine ring | | methyl | $Br^-$ |
| together form an imidazole ring | | methyl | $Br^-$ or $PF_6^-$ |
| together form a pyridine ring | | | $Br^-$ or $PF_6^-$ |
| together form | | | $Br^-$, $CF_3SO_3^-$ or $B(Ph)_4^-$ |

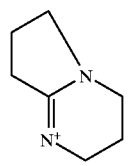

Preferred compounds of the formula Ia wherein Y is COOEt, n is 0 are

| $R_1$ | $R_2$ | $R_3$ | $X^-$ |
|---|---|---|---|
| hydrogen | n-octyl | n-octyl | $BF_4^-$ or $PF_6^-$ |
| methyl | methyl | n-octyl | $Br^-$ |
| methyl | methyl | benzyl | Br |
| methyl | n-octyl | n-octyl | $Br^-$, $BF_4^-$ or $PF_6^-$ |
| together form an imidazole ring | | methyl | $Br^-$ or $PF_6^-$ |
| together form a pyridine ring | | | $Br^-$ or $PF_6^-$ |

Preferred compounds of the formula Ia wherein Y is CN, n is 0 are

| $R_1$ | $R_2$ | $R_3$ | $X^-$ |
|---|---|---|---|
| hydrogen | n-octyl | n-octyl | $BF_4^-$ |
| methyl | methyl | methyl | $BF_4^-$ |
| methyl | n-octyl | n-octyl | $BF_4^-$ |

A further subject of the present invention is the use of a compound of the formulae (Ia), (Ib) or (Ic) in a radical initiated polymerisation process. The following Examples illustrate the invention in more detail. Temperatures are given in degrees Celsius (C.°); h: hour(s).

APPLICATION EXAMPLES

Thermal Polymerisation of Methacrylic Acid

General Description of the Experiments

To prevent any undesired reactions, solvents and monomers as well as reactants are purified by usual techniques before use. Polymerisations are carried out in sealed Schlenk tubes. The initial stock solution is prepared in a dry flask under argon and separated into portions as listed below. After addition of various amounts of addition-fragmentation agent (AFA), the magnetically stirred solutions are heated under inert atmosphere for a given period of time at a given temperature. After carrying out the reaction the solutions are cooled in an ice bath. The reaction mixture obtained is poured into a large excess of diethyl ether. The precipitated polymer is collected by filtration, dried under vacuum at 60–70° and characterised by Gel Permeation Chromatography (GPC) and NMR. The solid product is further purified by soxhlet extraction with acetone to remove traces of the unreacted AFA and dried under vacuum at 60–70°. Number-average molecular weight ($M_n$) and polydispersity ($M_w/M_n$=PD) are determined by GPC on the crude and purified products using poly (methacrylic acid) calibration standards. Moreover, the purified products are methylated with diazomethane for GPC characterisation in THF using poly (methyl methacrylate) calibration standards. The results are summarised in the following tables.

Example 1

Stock solution: methacrylic acid: 59.35 g, methanol: 119.41 g, AIBN: 1133.2 mg (entry 1–4); methacrylic acid: 46.22 g, methanol: 93.05 g, AIBN: 881.6 mg (entry 5–7). Polymerisation: 5 h at 60° (entry 1–4); 16 h at 60° (entry 5–7).

| | Solution [g] | AFA 1 [mg] | $M_n$ | PD | Polymer [g][a] | % Yield | $M_n$ (Ester) |
|---|---|---|---|---|---|---|---|
| 1 | 20.1 | 149.4 | 20287 | 2.2 | 5.52 | 82 | 19741 |
| 2 | 20.1 | 298.7 | 13581 | 2.0 | 5.17 | 76 | 13226 |
| 3 | 20.1 | 597.7 | 8800 | 1.8 | 4.70 | 68 | 8675 |
| 4 | 20.1 | 895.8 | 6773 | 1.7 | 4.32 | 62 | 6615 |
| 5 | 19.9 | 1492.9 | 4777 | 1.6 | 5.00 | 60 | 4678 |
| 6 | 20.3 | 2089.2 | 4215 | 1.5 | 5.31 | 59 | 4097 |
| 7 | 20.3 | 2686.7 | 3779 | 1.5 | 4.06 | 55 | — |

[a]Isolated polymer product after soxhlet extraction.

Example 2

Stock solution: methacrylic acid: 59.33 g, methanol: 119.45 g, AIBN: 11 33.4 mg (entry 1–4); methacrylic acid: 46.10 g, methanol: 92.98 g, AIBN: 881.4 mg (entry 5). Polymerisation: 5 h at 60° (entry 1–4); 16 h at 60° (entry 5).

| | Solution [g] | AFA 2 [mg] | $M_n$ | PD | Polymer [g][a] |
|---|---|---|---|---|---|
| 1 | 19.9 | 139.7 | 20169 | 2.1 | 5.10 |
| 2 | 20.2 | 278.1 | 13695 | 1.9 | 3.89 |
| 3 | 20.1 | 557.0 | 8316 | 1.8 | 2.09 |
| 4 | 20.1 | 835.8 | 6996 | 1.6 | 2.58 |
| 5 | 19.9 | 1393.0 | 5259 | 1.5 | 3.93 |

[a]Isolated polymer product after soxhlet extraction.

Example 3

Stock solution: methacrylic acid: 59.35 g, methanol: 119.41 g, AIBN: 11 33.2 mg (entry 1–4); methacrylic acid: 46.22 g, methanol: 93.05 g, AIBN: 881.6 mg (entry 5–7). Polymerisation: 5 h at 60° (entry 1–4); 16 h at 60° (entry 5–7).

| | Solution [g] | AFA 3 [mg] | $M_n$ | PD | Polymer [g][a] | % Yield | $M_n$ (Ester) |
|---|---|---|---|---|---|---|---|
| 1 | 20.1 | 165.3 | 18556 | 2.1 | 4.65 | 69 | — |
| 2 | 20.1 | 330.4 | 12055 | 1.9 | 5.21 | 76 | 12522 |
| 3 | 20.0 | 661.5 | 7323 | 1.7 | 4.41 | 63 | 7857 |
| 4 | 20.1 | 992.6 | 5587 | 1.7 | 4.26 | 60 | 6100 |
| 5 | 20.2 | 1654.4 | 3606 | 1.7 | 5.41 | 72 | 3942 |
| 6 | 20.3 | 2316.3 | 2921 | 1.6 | 5.33 | 69 | 3241 |
| 7 | 20.3 | 2978.2 | 2588 | 1.5 | 5.16 | 65 | 2913 |

[a]Isolated polymer product after soxhlet extraction.

Example 4

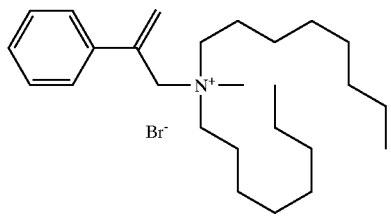

4

Stock solution: methacrylic acid: 59.33 g, methanol: 119.45 g, AIBN: 1133.4 mg (entry 1–4); methacrylic acid: 46.10 g, methanol: 92.98 g, AIBN: 881.4 mg (entry 5–7). Polymerisation: 5 h at 60° (entry 1–4); 16 h at 60° (entry 5–7).

|   | Solution [g] | AFA 4 [mg] | $M_n$ | PD | Polymer [g][a] | $M_n$ (Ester) |
|---|---|---|---|---|---|---|
| 1 | 19.9 | 173.5 | 17424 | 2.2 | 4.01 | — |
| 2 | 20.3 | 347.2 | 11331 | 2.0 | 3.80 | 12405 |
| 3 | 20.2 | 694.1 | 6836 | 1.9 | 3.07 | 8193 |
| 4 | 20.1 | 1040.9 | 4869 | 1.9 | 2.30 | 6096 |
| 5 | 20.1 | 1734.6 | 3517 | 1.8 | 4.15 | 4737 |
| 6 | 20.1 | 2428.6 | 2725 | 1.7 | 4.42 | 3876 |
| 7 | 20.0 | 3122.5 | 2372 | 1.7 | 3.14 | 3562 |

[a]Isolated polymer product after soxhlet extraction.

Example 5

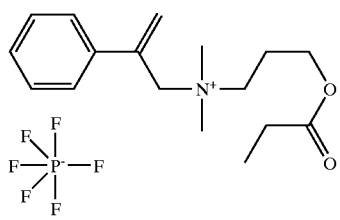

5

Stock solution: methacrylic acid: 59.41 g, methanol: 119.53 g, AIBN: 1133.1 mg (entry 1–4); methacrylic acid: 46.14 g, methanol: 92.97 g, AIBN: 881.4 mg (entry 5–7). Polymerisation: 5 h at 60° (entry 1–4); 16 h at 60° (entry 5–7).

|   | Solution [g] | AFA 5 [mg] | $M_n$ | PD | Polymer [g][a] | % Yield |
|---|---|---|---|---|---|---|
| 1 | 20.3 | 161.5 | 20628 | 2.0 | 4.83 | 72 |
| 2 | 20.3 | 323.0 | 13134 | 1.9 | 3.59 | 53 |
| 3 | 20.1 | 646.1 | 8932 | 1.7 | 2.79 | 40 |
| 4 | 20.2 | 969.1 | 6823 | 1.6 | 2.88 | 41 |
| 5 | 20.2 | 1615.2 | 3785 | 1.8 | 4.01 | 54 |
| 6 | 20.2 | 2261.3 | 2994 | 1.7 | 4.85 | 63 |
| 7 | 20.3 | 2907.4 | 2641 | 1.7 | 2.46 | 31 |

[a]Isolated polymer product after soxhlet extraction.

Example 6

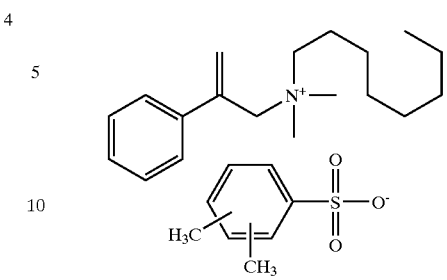

6

Stock solution: methacrylic acid: 59.39 g, methanol: 119.45 g, AIBN: 1133.0 mg (entry 1–4); methacrylic acid: 46.14 g, methanol: 92.97 g, AIBN: 881.4 mg (entry 5–7). Polymerisation: 5 h at 60° (entry 1–4); 16 h at 60° (entry 5–7).

|   | Solution [g] | AFA 6 [mg] | $M_n$ | PD | Polymer [g][a] | % Yield |
|---|---|---|---|---|---|---|
| 1 | 20.8 | 165.8 | 18888 | 2.3 | 5.70 |  |
| 2 | 20.9 | 330.6 | 12252 | 2.1 | 5.18 |  |
| 3 | 20.7 | 661.7 | 7221 | 2.0 | 4.65 |  |
| 4 | 20.8 | 992.6 | 5507 | 1.9 | 4.82 |  |
| 5 | 20.4 | 1762.0 | 3514 | 1.8 | 5.86 | 77 |
| 6 | 20.5 | 2467.1 | 2724 | 1.7 | 7.30 |  |
| 7 | 20.7 | 3171.6 | 2473 | 1.6 | 4.89 | 60 |

[a]Isolated polymer product after precipitation into diethyl ether (entries 1–4 and 6) and after soxhlet extraction (entries 5 and 7).

Example 7

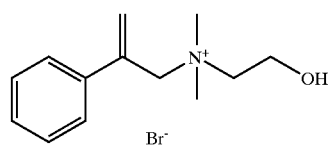

7

Stock solution: methacrylic acid: 39.63 g, methanol: 79.78 g, AIBN: 755.6 mg (entry 1–4); methacrylic acid: 46.14 g, methanol: 92.97 g, AIBN: 881.4 mg (entry 5/6). Polymerisation: 5 h at 60° (entry 1–4); 16 h at 60° (entry 5/6).

|   | Solution [g] | AFA 7 [mg] | $M_n$ | PD |
|---|---|---|---|---|
| 1 | 20.0 | 109.9 | 17982 | 2.0 |
| 2 | 20.1 | 219.9 | 11905 | 1.8 |
| 3 | 20.0 | 438.5 | 6617 | 1.7 |
| 4 | 20.3 | 658.6 | 5159 | 1.6 |
| 5 | 20.3 | 1097.6 | 3616 | 1.5 |
| 6 | 20.2 | 1975.2 | 2177 | 1.6 |

Example 8

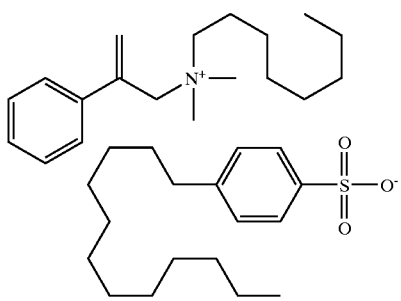

Stock solution: methacrylic acid: 59.39 g, methanol: 119.55 g, AIBN: 1133.0 mg (entry 1–4); methyacrylic acid: 46.30 g, methanol: 92.95 g, AIBN: 881.2 mg (entry 5–7). Polymerisation: 5 h at 60° (entry 1–4); 16 h at 60° (entry 5–7).

|   | Solution [g] | AFA 8 [mg] | $M_n$ | PD | Polymer [g][a] |
|---|---|---|---|---|---|
| 1 | 20.0 | 229.6 | 20311 | 2.4 | 5.35 |
| 2 | 20.2 | 460.8 | 13117 | 2.2 | 5.28 |
| 3 | 20.1 | 920.2 | 6756 | 1.9 | 4.18 |
| 4 | 20.1 | 1380.0 | 6111 | 1.9 | 3.89 |
| 5 | 20.5 | 2296.0 | 4143 | 1.7 | 6.10 |
| 6 | 20.4 | 3220.0 | 3647 | 1.7 | 5.64 |
| 7 | 20.4 | 4144.0 | 3452 | 1.5 | 2.09 |

[a]Isolated polymer product after precipitation into diethyl ether (entries 1–4 and 6) and after soxhlet extraction (entries 5 and 7).

Example 9

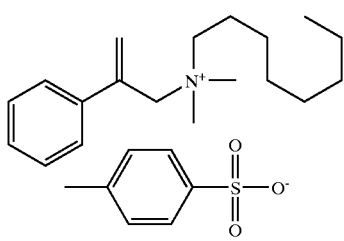

Stock solution: methacrylic acid: 59.39 g, methanol: 119.45 g, AIBN: 1133.0 mg (entry 1–4); methacrylic acid: 46.27 g, methanol: 93.10 g, AIBN: 881.5 mg (entry 5–7). Polymerisation: 5 h at 60° (entry 1–4); 16 h at 60° (entry 5–7).

|   | Solution [g] | AFA 9 [mg] | $M_n$ | PD | Polymer [g][a] |
|---|---|---|---|---|---|
| 1 | 20.7 | 170.6 | 16876 | 2.4 | 5.66 |
| 2 | 20.6 | 341.9 | 10928 | 2.2 | 5.47 |
| 3 | 20.6 | 683.5 | 6693 | 2.0 | 5.03 |
| 4 | 20.7 | 1025.4 | 4963 | 1.9 | 4.77 |
| 5 | 20.5 | 1708.2 | 3345 | 1.8 | 6.66 |
| 6 | 20.5 | 2391.5 | 2652 | 1.7 | 6.21 |
| 7 | 20.5 | 3074.9 | 2324 | 1.7 | 4.68 |

[a]Isolated polymer after precipitation into diethyl ether.

Example 10

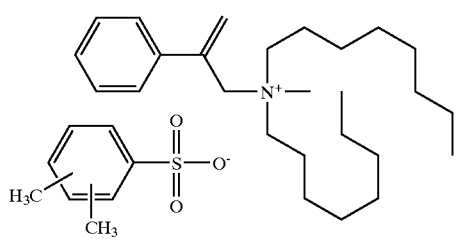

Stock solution: methacrylic acid: 59.39 g, methanol: 119.55 g, AIBN: 1133.0 mg (entry 1–4); methacrylic acid: 46.30 g, methanol: 92.95 g, AIBN: 881.2 mg (entry 5–7). Polymerisation: 5 h at 60° (entry 1–4); 16 h at 60° (entry 5–7).

|   | Solution [g] | AFA 10 [mg] | $M_n$ | PD | Polymer [g][a] |
|---|---|---|---|---|---|
| 1 | 20.1 | 213.9 | 18773 | 2.3 | 4.97 |
| 2 | 20.2 | 428.1 | 12356 | 2.1 | 5.02 |
| 3 | 20.1 | 855.3 | 7376 | 1.9 | 4.64 |
| 4 | 20.1 | 1282.9 | 5713 | 1.8 | 4.83 |
| 5 | 20.4 | 2138.2 | 3142 | 1.9 | 6.32 |
| 6 | 20.5 | 2994.4 | 2507 | 1.8 | 7.84 |
| 7 | 20.2 | 3849.8 | 2144 | 1.8 | 5.57 |

[a]Isolated polymer product after precipitation into diethyl ether (entries 1–4 and 6), and after soxhlet extraction (entries 5 and 7).

Example 11

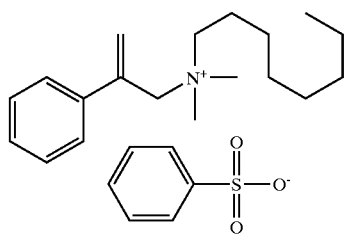

Stock solution: methacrylic acid: 59.36 g, methanol: 79.51 g, water 39.76 g, AIBN: 1133.1 mg. Polymerisation: 16 h at 60°.

| | Solution [g] | AFA 11 [mg] | $M_n$ | PD | Polymer [g][a] |
|---|---|---|---|---|---|
| 1 | 20.4 | 992.6 | 5280 | 2.0 | 6.76 |
| 2 | 20.2 | 1654.8 | 3708 | 1.8 | 6.95 |
| 3 | 20.2 | 2316.4 | 2993 | 1.7 | 6.30 |
| 4 | 20.3 | 2978.7 | 2575 | 1.6 | 7.46 |

[a]Isolated polymer product after precipitation into diethyl ether (entries 1, 2 and 4) and after soxhlet extraction (entry 3).

Example 12

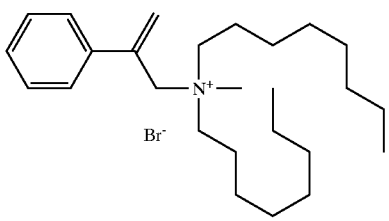

Stock solution: methacrylic acid: 59.36 g, methanol: 79.51 g, water 39.76 g, AIBN: 1133.1 mg. Polymerisation: 16 h at 60°.

| | Solution [g] | AFA 4 [mg] | $M_n$ | PD | Polymer [g][a] |
|---|---|---|---|---|---|
| 1 | 20.4 | 1040.2 | 5241 | 2.0 | 6.27 |
| 2 | 20.2 | 1734.5 | 3630 | 1.9 | 6.84 |
| 3 | 20.3 | 2429.5 | 2818 | 1.8 | 5.00 |
| 4 | 20.2 | 3122.4 | 2307 | 1.7 | 7.04 |

[a]Isolated polymer product after precipitation into diethyl ether (entries 1, 2 and 4) and after soxhlet extraction (entry 3).

Example 13

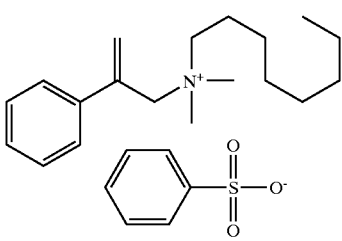

Stock solution: methacrylic acid: 59.41 g, 1-methoxy-2-propanol: 119.46 g, AIBN: 1133.2 mg. Polymerisation: 16 h at 60°.

| Solution [g] | AFA 3 [mg] | $M_n$ | PD |
|---|---|---|---|
| 20.2 | 1655.1 | 3496 | 1.7 |
| 20.4 | 2316.6 | 2804 | 1.7 |
| 20.3 | 2978.3 | 2619 | 1.6 |

Example 14

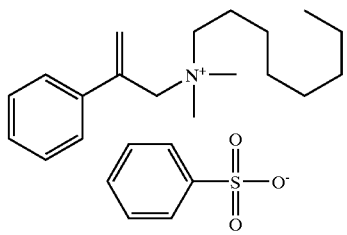

Stock solution: methacrylic acid: 59.4 g, 1-methoxy-2-propanol: 119.46 g, AIBN: 1133.2 mg. Polymerisation: 16 h at 60°.

| Solution [g] | AFA 4 [mg] | $M_n$ | PD |
|---|---|---|---|
| 20.0 | 1734.7 | 4000 | 1.8 |
| 20.2 | 2428.9 | 3092 | 1.8 |
| 20.1 | 3122.4 | 2430 | 1.7 |

Example 15

Stock solution: methacrylic acid: 29.67 g, acrylic acid: 29.67 g, methanol: 119.42 g, AIBN: 1233.2 mg. Polymerisation: 16 h at 60°.

| Solution [g] | AFA 3 [mg] | $M_n$ | PD |
|---|---|---|---|
| 20.1 | 993.0 | 4501 | 1.8 |
| 20.0 | 1654.9 | 3026 | 1.7 |
| 20.6 | 2316.3 | 2534 | 1.6 |
| 20.0 | 2978.5 | 2056 | 1.5 |

Example 16

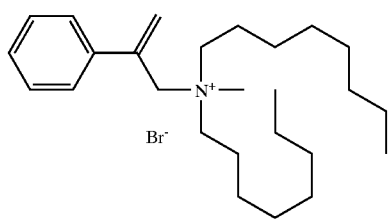

Stock solution: methacrylic acid: 29.67 g, acrylic acid: 29.67 g, methanol: 119.42 g, AIBN: 1233.2 mg. Polymerisation: 16 h at 60°.

| Solution [g] | AFA 4 [mg] | $M_n$ | PD |
|---|---|---|---|
| 20.1 | 1133.5 | 3937 | 1.8 |
| 20.0 | 1888.9 | 2763 | 1.7 |
| 20.0 | 2644.5 | 2178 | 1.6 |

Example 17

Stock solution: methacrylic acid: 90.00 g, methanol: 88.28 g, AIBN: 1 716.68 mg. Polymerisation: 3 h at 60°.

| Solution [g] | AFA 11 [mg] | $M_n$ | PD |
|---|---|---|---|
| 20.0 | 619.4 | 7514 | 1.9 |
| 20.0 | 1032.3 | 4963 | 1.8 |
| 20.0 | 1445.3 | 3837 | 1.7 |
| 20.0 | 1858.2 | 3448 | 1.6 |

Example 18

Stock solution: methacrylic acid: 90.00 g, methanol: 88.28 g, AIBN: 1 716.68 mg. Polymerisation: 3 h at 60°.

| Solution [g] | AFA 7 [mg] | $M_n$ | PD |
|---|---|---|---|
| 20.0 | 997.4 | 5134 | 1.8 |
| 20.0 | 1662.3 | 3642 | 1.6 |
| 20.0 | 2327.2 | 2845 | 1.6 |
| 20.0 | 2992.1 | 2477 | 1.5 |

Example 19

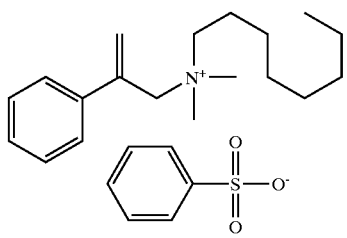

Stock solution: methacrylic acid: 164.93 g, methanol: 331.71 g, AIBN: 3147.5 mg. Polymerisation: 16 h at 60°.

| Solution [g] | AFA 3 [mg] | $M_n$ | PD | Polymer [g][a] | % Yield |
|---|---|---|---|---|---|
| 100.5 | 8.27 | 3799 | 1.7 | 29.2 | 78 |
| 100.5 | 14.89 | 2778 | 1.6 | 21.9 | 56 |

[a]Isolated polymer product after soxhlet extraction.

Stock solution: methacrylic acid: 33.07 g, methanol: 66.63 g, AIBN: 629.6 mg. Polymerisation: 16 h at 60°.

| Solution [g] | AFA 3 [mg] | $M_n$ | PD | $M_n$ (Ester) |
|---|---|---|---|---|
| 20.0 | 3640.2 | 2262 | 1.5 | 2687 |
| 20.1 | 4964.0 | 1788 | 1.5 | 2378 |

Stock solution: methacrylic acid: 50.03 g, methanol: 49.19 g, AIBN: 953.5 mg. Polymerisation: 4 h at 60°.

| Solution [g] | AFA 3 [mg] | $M_n$ | PD |
|---|---|---|---|
| 20.7 | 1503.9 | 6309 | 1.9 |
| 20.7 | 3008.5 | 3842 | 1.7 |

Example 20

Stock solution: methacrylic acid: 164.93 g, methanol: 331.71 g, AIBN: 3147.5 mg. Polymerisation: 16 h at 60°.

| Solution [g] | AFA 4 [mg] | $M_n$ | PD | Polymer [g][a] | % Yield |
|---|---|---|---|---|---|
| 100.5 | 8.67 | 3377 | 1.8 | 29.1 | 76 |
| 100.2 | 15.61 | 2491 | 1.6 | 20.1 | 47 |

[a]Isolated polymer product after soxhlet extraction.

Stock solution: methacrylic acid: 33.07 g, methanol: 66.63 g, AIBN: 629.6 mg. Polymerisation: 16 h at 60°.

| Solution [g] | AFA 4 [mg] | $M_n$ | PD | $M_n$ (Ester) |
|---|---|---|---|---|
| 20.3 | 3817.0 | 2031 | 1.6 | 3271 |
| 19.7 | 5204.8 | 1740 | 1.6 | 2978 |

Stock solution: methacrylic acid: 50.01 g, methanol: 49.15 g, AIBN: 953.9 mg. Polymerisation: 4 h at 60°.

| Solution [g] | AFA 4 [mg] | $M_n$ | PD |
|---|---|---|---|
| 21.1 | 1576.8 | 6637 | 2.1 |
| 20.7 | 3154.4 | 3727 | 1.9 |

Example 21

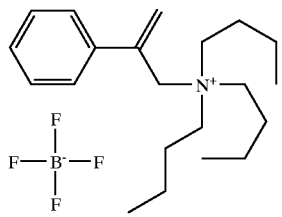

Stock solution: methacrylic acid: 164.92 g, methanol: 331.74 g, AIBN: 3147.5 mg. Polymerisation: 16 h at 60°.

| Solution [g] | AFA 1 [mg] | $M_n$ | PD | Polymer [g][a] | % Yield |
|---|---|---|---|---|---|
| 100.7 | 7.46 | 4632 | 1.7 | 25.64 | 68 |
| 100.5 | 13.43 | 3447 | 1.5 | 24.47 | 59 |

[a]Isolated polymer product after soxhlet extraction.

Stock solution: methacrylic acid: 59.47 g, methanol: 119.50 g, AIBN: 1132.9 mg. Polymerisation: 16 h at 60°.

| Solution [g] | AFA 1 [mg] | $M_n$ | PD | $M_n$ (Ester) |
|---|---|---|---|---|
| 20.3 | 3283.2 | 3319 | 1.4 | 3503 |
| 20.6 | 4477.3 | 3161 | 1.3 | 3298 |

Example 22

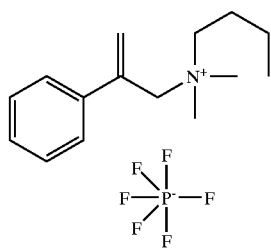

Stock solution: methacrylic acid: 164.92 g, methanol: 331.74 g, AIBN: 3147.5 mg. Polymerisation: 16 h at 60°.

| Solution [g] | AFA 2 [mg] | $M_n$ | PD | Polymer [g][a] | % Yield |
|---|---|---|---|---|---|
| 101.5 | 6.96 | 4408 | 1.7 | 23.96 | 67 |
| 100.5 | 12.53 | 3378 | 1.5 | 20.97 | 57 |

[a]Isolated polymer product after soxhlet extraction.

Stock solution: methacrylic acid: 59.47 g, methanol: 119.50 g, AIBN: 1132.9 mg. Polymerisation: 16 h at 60°.

| Solution [g] | AFA 2 [mg] | $M_n$ | PD |
|---|---|---|---|
| 20.3 | 3064.2 | 2615 | 1.5 |
| 20.2 | 4178.7 | 2030 | 1.5 |

Stock solution: methacrylic acid: 40.14 g, methanol: 39.34 g, AIBN: 762.8 mg. Polymerisation: 3.5 h at 60°.

| Solution [g] | AFA 2 [mg] | $M_n$ | PD |
|---|---|---|---|
| 20.8 | 1266.1 | 8057 | 1.8 |
| 20.6 | 2110.2 | 6238 | 1.7 |
| 20.6 | 2954.6 | 5529 | 1.6 |

Stock solution: methacrylic acid: 33.11 g, methanol: 66.02 g, VA-086 [=2,2'-azobis(2-methyl-N-(2-hydroxyethyl)propionamide]: 1105.7 mg. Polymerisation: 4 h at 60°.

| Solution [g] | AFA 2 [mg] | $M_n$ | PD |
|---|---|---|---|
| 20.8 | 278.3 | 16567 | 2.1 |
| 20.8 | 835.4 | 7196 | 1.9 |
| 20.8 | 1392.9 | 5091 | 1.8 |
| 20.6 | 1950.2 | 4013 | 1.7 |

Example 23

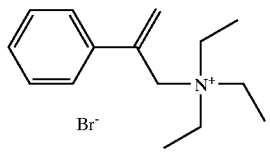

12

Stock solution: methacrylic acid: 62.69 g, methanol: 126.10 g, AIBN: 1195.8 mg. Polymerisation: 5 h at 60°.

| Solution [g] | AFA 12 [mg] | $M_n$ | PD |
|---|---|---|---|
| 20.6 | 686.0 | 7489 | 1.8 |
| 20.5 | 914.7 | 6099 | 1.8 |
| 20.1 | 1143.3 | 4663 | 1.9 |
| 20.4 | 1372.0 | 4261 | 1.7 |

Example 24

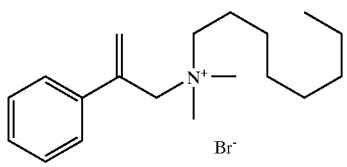

13

Stock solution: methacrylic acid: 62.65 g, methanol: 126.13 g, AIBN: 1195.7 mg. Polymerisation: 5 h at 60°.

| Solution [g] | AFA 13 [mg] | $M_n$ | PD |
|---|---|---|---|
| 20.0 | 815.0 | 6200 | 1.7 |
| 20.1 | 1086.7 | 4908 | 1.6 |
| 20.3 | 1358.4 | 4351 | 1.7 |
| 20.1 | 1630.1 | 3987 | 1.6 |

Stock solution: methacrylic acid: 50.01 g, methanol: 49.15 g, AIBN: 953.9 mg. Polymerisation: 4 h at 60°.

| Solution [g] | AFA 13 [mg] | $M_n$ | PD |
|---|---|---|---|
| 20.8 | 1234.8 | 6877 | 1.8 |
| 20.8 | 2469.8 | 3892 | 1.7 |

Example 25

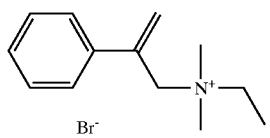

14

Stock solution: methacrylic acid: 62.71 g, methanol: 126.18 g, AIBN: 1196.1 mg. Polymerisation: 5 h at 60°.

| Solution [g] | AFA 14 [mg] | $M_n$ | PD |
|---|---|---|---|
| 20.1 | 621.5 | 5800 | 1.7 |
| 20.2 | 828.6 | 4923 | 1.7 |
| 20.1 | 1243.0 | 3117 | 1.7 |

Stock solution: methacrylic acid: 33.11 g, water 65.97 g, V-50 [=2,2'-azobis(2-amidinopropane)dihydrochloride] 1039.4 mg. Polymerisation: 2.4 h at 60°.

| Solution [g] | AFA 14 [mg] | $M_n$ | PD |
|---|---|---|---|
| 20.3 | 621.8 | 6117 | 2.0 |
| 20.5 | 1035.7 | 3561 | 1.9 |

Example 26

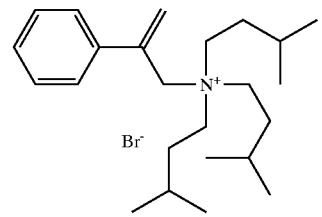

15

Stock solution: methacrylic acid: 33.05 g, methanol: 66.49 g, AIBN: 629.5 mg. Polymerisation: 4 h at 60°.

| Solution [g] | AFA 15 [mg] | $M_n$ | PD |
|---|---|---|---|
| 120.4 | 977.5 | 6385 | 1.9 |
| 19.9 | 1300.5 | 5047 | 1.9 |
| 20.3 | 1632.8 | 4303 | 1.8 |
| 20.4 | 1951.9 | 3731 | 1.8 |

Stock solution: methacrylic acid: 50.03 g, methanol: 49.19 g, AIBN: 953.5 mg. Polymerisation: 4 h at 60°.

| Solution [g] | AFA 15 [mg] | $M_n$ | PD |
|---|---|---|---|
| 20.4 | 1476.5 | 7749 | 1.9 |
| 20.7 | 2959.2 | 4923 | 1.7 |

Example 27

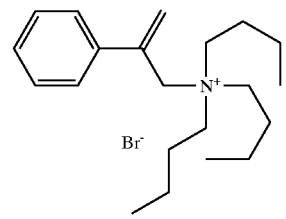

16

Stock solution: methacrylic acid: 65.98 g, methanol: 132.75 g, AIBN: 1259.0 mg. Polymerisation: 5 h at 60°.

| Solution [g] | AFA 16 [mg] | $M_n$ | PD |
|---|---|---|---|
| 20.1 | 879.3 | 6149 | 1.9 |
| 20.2 | 1172.4 | 4040 | 1.9 |
| 20.2 | 1759.9 | 3300 | 1.8 |

What is claimed is:

1. A composition comprising
   a) acrylic acid or oligomer of acrylic acid or a monomer or oligomer of monomers of an acid derivative of acrylic acid
      wherein the monomer is selected from the group consisting of methacrylic acid, 2-trifluoromethylpropenoic acid, 2-(4-benzyloxy-3-methoxyphenyl)acrylic acid, 2-benzylacrylic acid, itaconic acid, monomethyl, monoethyl, mono-isopropyl, mono-n-butyl, mono-n-dodecyl, mono-2-ethylhexyl, monotrifluoroethyl or monohexafluoroisopropyl itaconate, butene-1,2,3-tricarboxylic acid and mixtures thereof;
   or a mixture of
   acrylic acid, oligomer of acrylic acid or said monomer or said oligomer of acid derivative of acrylic acid and
   an ethylenically unsaturated monomer or oligomer wherein the ethylenically unsaturated monomer or monomer precursor to said oligomer is selected from the group consisting of ethylene, propylene, n-butylene, isobutylene, isoprene, styrene, substituted styrene, conjugated dienes, acrolein, vinyl acetate, vinylpyrrolidone, vinylimidazole, maleic anhydride, (alkyl)acrylic acid anhydrides, (alkyl)acrylic acid salts, (alkyl)acrylic esters, (meth)acrylonitriles, (alkyl)acrylamides, vinyl halides and vinylidene halides;
   b) at least one radical initiator which forms a radical upon heating or upon irradiation with (UV) light in the range from 305 nm to 450 nm; and
   c) a compound of the formulae (Ia), (Ib) or (Ic)

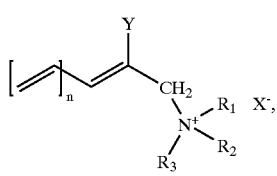

(Ia)

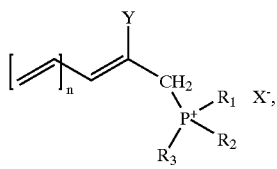

(Ib)

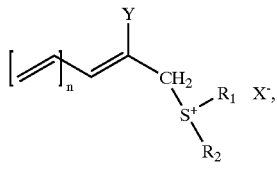

(Ic)

wherein
Y represents a group that activates nucleophilic addition reactions at the adjacent double bond;

$X^-$ represents halogen or the anion of an aliphatic or aromatic monocarboxylic or dicarboxylic acid of 1–12 carbon atoms, of a monovalent or divalent oxo acid or of a complex acid;

n represents 0 or 1;

$R_1$, $R_2$, $R_3$ independently of one another represent hydrogen, $C_1$–$C_{18}$alkyl, $C_3$–$C_{18}$alkyl interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_3$–$C_{18}$alkyl interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl and $C_3$–$C_{12}$cycloalkyl containing at least one nitrogen or oxygen atom, which are substituted with at least one substituent selected from the group consisting of $NO_2$, halogen, amino, hydroxy, cyano, carboxy, $C_1$–$C_4$alkoxy, $C_1$–$C_4$alkylthio, $C_1$–$C_4$alkylamino, di($C_1$–$C_4$alkyl)amino and —O—C(=O)—$C_1$–$C_{18}$alkyl; or phenyl or naphthyl or phenyl and naphthyl substituted with at least one substituent selected from the group consisting of $C_1$–$C_4$alkyl, $C_1$–$C_4$alkoxy, $C_1$–$C_4$alkylthio, halogen, cyano, hydroxy, carboxy, $C_1$–$C_4$alkylamino and di($C_1$–$C_4$alkyl)amino; or $R_1$ and $R_2$ together with the linking N, P or S-heteroatoms form a $C_3$–$C_{12}$ heterocycloalkyl radical; or or $R_1$ and $R_2$ together form the groups:

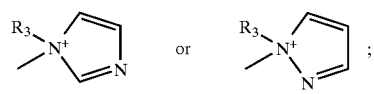

or $R_1$, $R_2$ and $R_3$ together form the groups

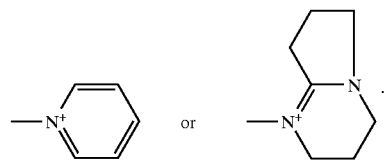

2. A composition according to claim 1, comprising a compound of the formula (Ia) with n=1.

3. A composition according to claim 1, wherein
$R_1$, $R_2$, $R_3$ independently of one another represent $C_1$–$C_{12}$alkyl, $C_1$–$C_{12}$alkyl substituted by cyano or hydroxy, $C_3$–$C_{12}$alkyl interrupted by at least one nitrogen or oxygen atom, benzyl or phenyl, or benzyl and phenyl which are substituted by at least one substituent selected from the group consisting of $C_1$–$C_4$alkyl, $C_1$–$C_4$alkoxy, $C_1$–$C_4$alkylthio, halogen, cyano, hydroxy and carboxy.

4. A composition according to claim 1, wherein
Y represents CN; phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;
—C(=O)$OR_4$ with $R_4$ being hydrogen or $C_1$–$C_{18}$alkyl;
—C(=O)$R_5$ with $R_5$ being hydrogen, halogen, $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—C(=O)NR$_6$R$_7$ with R$_6$ and R$_7$ independently of one another being hydrogen or $C_1$–$C_{18}$alkyl;

—S(=O)R$_8$ with R$_8$ being $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—S(=O)$_2$R$_9$ with R$_9$ being hydroxy, $C_1$–$C_{18}$alkyl, $C_1$–$C_{18}$alkoxy, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—P(=O)R$_{10}$R$_{11}$ with R$_{10}$ and R$_{11}$ independently of one another being $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—P(=O)(OR$_{12}$)$_2$ with R$_{12}$ being $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino;

—P(=O)OH(NR$_{13}$R$_{14}$)$_2$ with R$_{13}$ and R$_{14}$ independently of one another being $C_1$–$C_{18}$alkyl, phenyl or naphthyl or phenyl and naphthyl which are substituted with a substituent selected from the group consisting of $C_1$–$C_4$alkyl, $C_1$–$C_4$alkoxy, $C_1$–$C_4$alkylthio, halogen, nitro, cyano, hydroxy, carboxy, $C_1$–$C_4$alkylamino and di($C_1$–$C_4$alkyl)amino.

5. A composition according to claim 4, wherein

Y represents CN, —C(=O)OR$_4$, phenyl or phenyl substituted by at least one substituent selected from the group consisting of $C_1$–$C_4$alkyl, $C_1$–$C_4$alkoxy, $C_1$–$C_4$alkylthio, halogen, cyano, hydroxy, carboxy, $C_1$–$C_4$alkylamino and di($C_1$–$C_4$alkyl)amino and R$_4$ represents $C_1$–$C_8$alkyl.

6. A composition according to claim 1, wherein

X$^-$ represents the anion of an aliphatic or aromatic monocarboxylic or dicarboxylic acid from 1–12 carbon atoms, of a monovalent or divalent oxo acid or of a complex acid.

7. A composition according to claim 1, wherein the acid monomer is acrylic acid or methacrylic acid.

8. A process for preparing an acid oligomer, an acid cooligomer, an acid polymer or an acid copolymer by free radical polymerisation of a) acrylic acid or oligomer of acrylic acid or a monomer or oligomer of monomers of an acid derivative of acrylic acid wherein the monomer is selected from the group consisting of methacrylic acid, 2-trifluoromethylpropenoic acid, 2-(4-benzyloxy-3-methoxyphenyl)acrylic acid, 2-benzylacrylic acid, itaconic acid, monomethyl, monoethyl, mono-isopropyl, mono-n-butyl, mono-n-dodecyl, mono-2-ethylhexyl, monotrifluoroethyl or monohexafluoroisopropyl itaconate, butene-1,2,3-tricarboxylic acid and mixtures thereof;

or a mixture of acrylic acid, oligomer of acrylic acid or said monomer or said oligomer of acid derivative of acrylic acid and an ethylenically unsaturated monomer or oligomer wherein the ethylenically unsaturated monomer or monomer precursor to said oligomer is selected from the group consisting of ethylene, propylene, n-butylene, isobutylene, isoprene, styrene, substituted styrene, conjugated dienes, acrolein, vinyl acetate, vinylpyrrolidone, vinylimidazole, maleic anhydride, (alkyl)acrylic acid anhydrides, (alkyl) acrylic acid salts, (alkyl)acrylic esters, (meth) acrylonitriles, (alkyl)acrylamides, vinyl halides and vinylidene halides;

which comprises (co)polymerising acrylic acid, said monomers or said oligomers or said mixtures in the presence of b) a radical initiator which forms a radical upon heating or upon irradiation with (UV) light from 305 nm to 450 nm, and c) a compound of the formulae (Ia), (Ib) or (Ic) as defined in claim 1, by subjecting the mixture to heat or electromagnetic radiation with a wavelength of the range from 305 nm to 450 nm.

9. An acid oligomer/polymer of the formula IIa, IIb or IIc

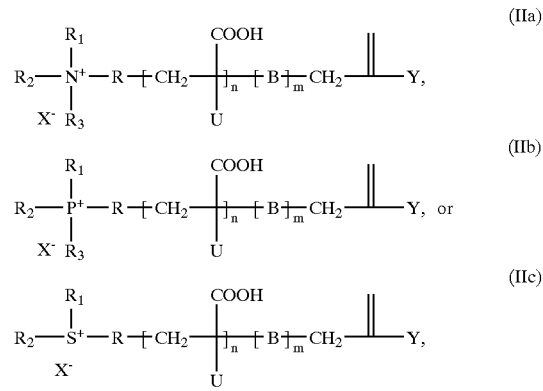

wherein

X$^-$ and Y are as defined in claim 1;

R$_1$, R$_2$, R$_3$ are as defined in claim 1;

R represents the direct bond or linear or branched $C_1$–$C_5$alkylene; with the proviso that when R is $C_1$–$C_5$alkylene, one of the residues R$_1$, R$_2$ or R$_3$ is hydrogen;

U represents hydrogen, methyl, trifluoromethyl, carboxymethyl, methoxycarbonylmethyl, ethoxycarbonylmethyl, trifluoroethoxycarbonylmethyl, isopropoxycarbonylmethyl, hexafluoroisopropoxycarbonylmethyl, n-butoxycarbonylmethyl, n-dodecyloxycarbonylmethyl, 2-ethylhexoxycarbonylmethyl, perfluorooctyloxycarbonylmethyl, 1,2-dicarboxyeth-1-yl, benzyl or 4-benzyloxy-3-methoxyphenyl;

B represents a residue derived from the ethylenically unsaturated comonomer;

m ≧ 0;

n > 0;

and when either or both of m and n are greater than 0, the repeat units are identical or different.

10. An acid oligomer/polymer according to claim 9 of the formulae IIa-a and IIa-b

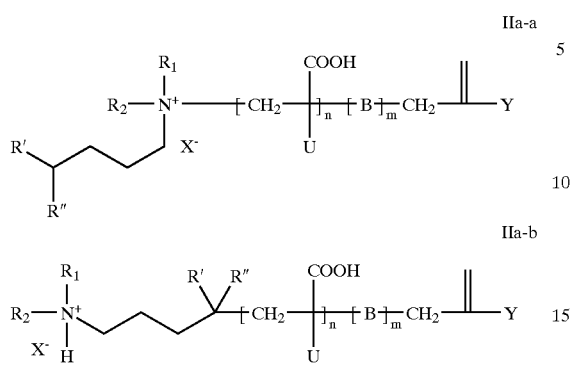

wherein $R_1$, $R_2$, U, B, $X^-$, Y, m and n are as defined in claim 10 and R' and R" each independently of one another represent $C_1$–$C_{18}$alkyl, $C_3$–$C_{18}$alkyl interrupted by at least one nitrogen or oxygen atom, $C_3$–$C_{18}$alkenyl, $C_3$–$C_{18}$alkynyl or $C_7$–$C_9$phenylalkyl; or $C_1$–$C_{18}$alkyl, $C_3$–$C_{18}$alkyl interrupted by at least one nitrogen or oxygen atom, $C_3$–$C_{18}$alkenyl, $C_3$–$C_{18}$alkynyl or $C_7$–$C_9$phenylalkyl, which are substituted with a substituent selected from the group consisting of $NO_2$, halogen, amino, hydroxy, cyano, carboxy, $C_1$–$C_4$alkoxy, $C_1$–$C_4$alkylthio, $C_1$–$C_4$alkylamino, di($C_1$–$C_4$alkyl)amino and the group —O—C(=O)—$C_1$–$C_{18}$alkyl.

* * * * *